United States Patent
Azoulay et al.

(10) Patent No.: US 8,242,297 B2
(45) Date of Patent: Aug. 14, 2012

(54) TRANSITION METAL INITIATORS SUPPORTED BY KETONE DIIMINE LIGANDS FOR THE HOMOPOLYMERIZATION OF OLEFINS AND THE COPOLYMERIZATION OF OLEFINS WITH POLAR COMONOMERS

(75) Inventors: Jason D. Azoulay, Goleta, CA (US); Yanika Schneider, Goleta, CA (US); Guillermo C. Bazan, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 560 days.

(21) Appl. No.: 12/435,706

(22) Filed: May 5, 2009

(65) Prior Publication Data
US 2009/0299020 A1    Dec. 3, 2009

Related U.S. Application Data

(60) Provisional application No. 61/128,174, filed on May 19, 2008.

(51) Int. Cl.
C07F 15/04 (2006.01)
C07F 15/02 (2006.01)
C07F 15/06 (2006.01)
(52) U.S. Cl. .............. 556/138; 556/136; 556/137
(58) Field of Classification Search ............ 556/138, 556/136, 137
See application file for complete search history.

(56) References Cited

U.S. PATENT DOCUMENTS
5,886,224 A  3/1999  Brookhart et al.
6,369,194 B1  4/2002  Wasserman
6,670,297 B1  12/2003  Brookhart et al.
7,205,422 B2  4/2007  Norman

OTHER PUBLICATIONS

Yokota, S.; Tachi, Y.; Itoh, S. Inorg. Chem., 2002, 41, 1342-1344.*
Byers, P. K.; Canty, A. J.; Skelton, B. W.; White, A. H. Organometallics, 1990, 9, 826-832.*
Byers et al., Organometallics, 1990, 9, 826-832.*
Done et al., J. Organomet. Chem., 2000, 607, 78-92.*
Batten et al., Inorg. Chim. Acta, 2006, 359, 1710-1724.*
Yokota et al., Inorg. Chem., 2002, 41, 1342-1344.*
S. D. Ittel, L. K. Johnson, M. Brookhart, Chem. Rev. 2000, 100, 1169-1203.
L. S. Boffa, B. M. Novak, Chem. Rev. 2000, 100, 1479-1493.
M. J. Yanjarappa, S. Sivaram, Prog. Polym. Sci. 2002, 27, 1347-1398.
S. Mecking, A. Held, F. M. Bauers, Angew. Chem., Int. Ed. 2002, 41, 544-561.
V. C. Gibson, S. K. Spitzmesser, Chem. Rev. 2003, 103, 283-315.

(Continued)

Primary Examiner — Rip A. Lee
(74) Attorney, Agent, or Firm — Berliner & Associates

(57) ABSTRACT

Metal-ligand combination initiators are provided which yield organometallic complexes capable of the polymerization of olefins to high molecular weight polymers. Additionally, these initiators also enable the copolymerization of olefins with functionalized comonomers. These organometallic complexes comprise of a late transition metal with a neutral chelating ligand that contains a Lewis basic functionality in conjugation with an electronically delocalized conduit extending from the metal to the functionality. This structural feature results in a highly active complex, which generates high molecular weight polymers with unique microstructures. Under particular conditions, the organometallic complexes provide for the living polymerization of monomers and comonomers.

17 Claims, 7 Drawing Sheets

OTHER PUBLICATIONS

Mitani, M.; Furuyama, R.; Mohri, J.-I.; Saito, J.; Ishii, S.; Terao, H.; Nakano, T.; Tanaka, H.; Fujita, T. *J. Am. Chem. Soc.* 2003, 125, 4293.
Saito, J.; Mitani, M.; Onda, M.; Mohri, J.-I.; Ishii, S.-I.; Yoshida, Y.; Nakano, T. H.; Tanaka, T.; Kojoh, S.-I.; Kashiwa, N.; Fujita, T. *Macromol. Rapid Commun.* 2001, 22, 1072.
Benedikt, G.M.; Elce, E.; Goodall, B. L.; Kalamarides, H. A.; McIntosh, L. H. III; Rhodes, L. F.; Selvy, K. T.; Andes, C.; Oyler, K.; Sen, A. *Macromolecules* 2002, 35, 8978.
Gottfried, A. C.; Brookhart, M. *Macromolecules*, 2003, 36, 3085.
Kleinschmidt, R.; Griebenow, Y.; Fink, G. *Journal of Molecular Catalysis A: Chemical* 2000, 157, 83.
Pellecchia, C.; Mazzeo, M.; Pappalardo, D: *Macromol. Rapid Commun.* 1998, 19, 651.
Guerra, G.; Longo, P.; Cavallo, L.; Corradini, P.; Resconi, L. *J. Am. Chem. Soc.* 1997, 119, 4394.
Choo, T. N.; Waymouth, R. M. *J. Am. Chem. Soc.* 2002, 124, 4188.
Nomura, K.; Oya, K.; Imanishi, Y. *Journal of Molecular Catalysis A: Chemical* 2001, 174, 127.
Schaverien, C. J.; Ernst, R.; Schut, P.; Dall'Occo, T. *Organometallics* 2001, 20, 3436.
J. M. Rose, A. E. Cherian, G. W. Coates. *J. Am. Chem. Soc.* 2006, 128, 4186-4187.
Johnson, L. K.; Mecking, S.; Brookhart, M. *J. Am. Chem. Soc.* 1996, 118, 267.
Mecking, S.; Johnson, L. K.; Wang, L.; Brookhart, M.; *J. Am. Chem. Soc.* 1998, 120, 888.
Younkin, T. R.; Connor, E. F.; Henderson, J. I.; Freidrich, S. K.; Grubbs, R. H.; Bansleben, D. A. *Science* 2000, 287, 460.
Connor, E. F.; Younkin, T. R.; Henderson, J. I.; Hwang, S.; Grubbs, R. H.; Roberts, W. P.; Litzau, J. J. *J. Polym Sci. Part A: Polym. Chem.* 2002, 40, 2842.
S. J. Diamanti, P. Ghosh, F. Shimizu, G. C. Bazan, *Macromolecules* 2003, 36, 9731-9735.
S. J. Diamanti, V. Khanna, A. Hotta, D. Yamakawa, F. Shimizu, E. J. Kramer, G. H. Frederickson, G. C. Bazan, *J. Am. Chem. Soc.* 2004, 126, 10528-10529.
R. C. Coffin, S. J. Diamanti, A. Hotta, V. Khanna, E. J. Kramer, G. H. Fredrickson, G. C. Bazan, *Chem. Commun.* 2007, 3550-3552.
Mohring V. M.; Fink G. *Angew. Chem:, Int. Ed. Engl.* 1985, 24, 1001.
Guan Z.,; Cotts P. M.; McCord E. F.; McClain S. J. *Science* 1999, 283, 2059-2062.
Held A.; Bauers F. M.; Mecking S. *Chem. Commun.* 2000, 301-302.
Bauers F. M.; Mecking S. *Macromolecules* 2001, 34, 1165-1171.
Korthals B.; Schnetmann I. G.; Mecking S. *Organometallics* 2007, 26, 1311-1316.
Bonnet, M. C.; Dahan, F.; Ecke, A.; Keim, W.; Schultz, R. P.; Tkatchenko, I. J. *J. Chem. Soc., Chem. Commun.* 1994, 615-616.
Komon, Z. J.; Bu, X.; Bazan, G. C. *J. Am. Chem. Soc.* 2000, 122, 1830-1831.
Komon, Z. J.; Bu, X.; Bazan, G. C. *J. Am. Chem. Soc.* 2000, 122, 12379-12380.
Lee, B. Y.; Bazan, G.C.; Vela, J; Komon, Z. J.; Bu, X. *J. Am. Chem. Soc.* 2001, 123, 5352-5353.
Chen, Y.; Wu, G.; Bazan, G.C. *Angew. Chem., Int. Ed. Engl.* 2005, 44, 1108-1112.
Kwon, H. Y.; Lee, S. Y.; Lee, B. Y.; Shin, D. M.; Chung, Y. K. *Dalton Transactions* 2004, 921-928.
Shim, C. B.; Kim, Y. H.; Lee, B.Y.; Shin, D. M; Chung, Y. K. *J. Organomet. Chem.* 2003, 675, 72-76.
Kim, Y. H.; Kim, T. H.; Lee, B. Y.; Woodmandee, D.; Bu, X; Bazan, G.C. *Organometallics* 2002, 21, 3082-3084.
Shim, C.B.; Kim, Y. H.; Lee, B.Y.; Dong, Y.; Yun. H. *Organometallics* 2003, 22, 4272-4280.
Lee, B.Y.; Bu, X., Bazan, G.C. *Organometallics* 2001, 20, 5425-5431.
S. Yokota, Y. Tachi, S. Itoh *Inorg. Chem.* 2002, 41, 1342-1344.
J. Feldman, S. J. McLain, A. Parthasarathy, W. J. Marshall, J. C. Calabrese, S. D. Arthur, *Organometallics* 1997, 16, 1514-1516.
Domski, G.J.; Rose, J.M.; Coates, G.W.; Bolig, A.D.; Brookhart, M. *Prog. Polym. Sci.* 2007, 32, 30-92.
Coates, G.W.; Hustad, P.D.; Reinartz, S. *Angew. Chem., Int. Ed. Engl.* 2002, 41, 2237-2257.
Johnson, L. K.; Mecking, S.; Brookhart, M. *J. Am. Chem. Soc.* 1996, 118, 267-268.
Berkefeld, A.; Mecking, S. *Angew. Chem. Int. Ed.* 2008, 47, 2-7.
Johnson, L. K.; Killian, C. M.; Brookhart, M. *J. Am. Chem. Soc.* 1995; 117, 6414-6415.
Leatherman, M. D.; Svedja, S. A; Johnson, L. K.; Brookhart, M. *J. Am. Chem. Soc.* 2003, 125, 3068-3081.
Meinhard, D.; Wegner, M.; Kipiani, G.; Hearley, A.; Reuter, P.; Fischer, S.; Marti, O.; Rieger, B. *J. Am. Chem. Soc.* 2007, 129, 9182-9191.
Killian, C. M.; Tempel, D. J.; Johnson, L. K.; Brookhart, M. *J. Am. Chem. Soc.* 1996, 118, 11664-11665.
Rose, J.M.; Deplace, F.; Lynd, N.A.; Wang, Z.; Hotta, A.; Lobkovsky, E.B..Kramer, E.J; Coates, G.W. *Macromolecules* 2008, 41, 9548-9555.
Azoulay, J.D.; Rojas, R.S.; Serrano, A.V.; Ohtaki, H.; Galland, G.B.; Bazan, G.C. *Angew. Chem., Int. Ed. Engl.* 2009, 48, 1089-1092.
Chen, E.Y-X.; Marks, T.J.; *Chem. Rev.* 2000, 100, 1391-1434.
Tian, J.; Hustad, D.; Coates, G.W. *J. Am. Chem. Soc.* 2001, 123, 5134-5135.
Mitani, M.; Furuyama, R.; Mohri, J-I.; Saito, J.; Ishii, S.-I.; Terao, H.; Kashiwa, N.; Fujita, T. *J. Am. Chem. Soc.* 2002, 124, 7888-7889.
Hasan, T.; Ioku, A.; Nishii, K.; Shiono, T.; Ikeda, T.; *Macromolecules* 2001, 34, 3142-3145.
Busico, V.; Cipullo, R.; Cutillo, F.; Friederichs, N.; Ronca, S.; Wang, B. *J. Am. Chem. Soc.* 2003, 125, 12402-12403.
Pappalardo, D.; Mazzeo, M.; Antinucci, S.; Pellechia, C. *Macromolecules* 2000, 33, 9483-9487.
Pellechia, C.; Zambelli, A.; *Macromol. Rapid. Commun.* 1996, 17, 333-338.
G.B. Galland, L. P. Da Silva, M. L. Dias, G. L. Crosetti, C.M. Ziglio, C. A. L. Filgueiras, *J. Polym. Sci: Part A: Polym. Chem.* 2004, 42, 2171-2178.
F.F.N. Escher, G.B. Galland, *J. Polym. Sci. Part A: Polym. Chem.* 2004, 42, 2474-2482.
M.L. Dias, L.P. Da Silva, G.L. Crosetti, G.B. Galland, A.L. Filgueiras, C.M. Ziglio, *J. Polym. Sci. Part A: Polym. Chem.* 2006; 44, 458-466.
Hagimoto, H.; Shiono, T.; Ikeda, T. *Macromoleicules*, 2002, 35, 5744.
Obera, Y.; Stern, C. L.; Marks, T. J. *Organometallics* 1997, 16, 2503.
Cherian, A. E.; Rose, J. M.; Lobkovsky, E. B.; Coates, G. W.; *J. Am. Chem. Soc.* 2005, 127, 13770-13771.

\* cited by examiner

| Reaction | Cat. total (μmol) | Solvent | Vol (mL) | Cocat. | Eq. | Mon. | T (°C) | Time (min) | P (MPag) | Yield (g) | Activity$^a$ | $M_n$ x $10^3$ | $M_w$ x $10^3$ | PDI |
|---|---|---|---|---|---|---|---|---|---|---|---|---|---|---|
| 1 | 25 | Toluene | 1000 | MAO | 1000 | ETY | 35 | 30 | 2.1 | 25 | 2000 | 986 | 463 | 2.13 |
| 2 | 25 | Toluene | 1000 | MAO | 2500 | ETY | 35 | 30 | 2.1 | 27 | 2160 | 958 | 492 | 1.95 |
| 3 | 25 | Toluene | 1000 | MMAO | 1000 | ETY | 35 | 3 | 2.1 | 12 | 9600 | 279 | 112 | 2.50 |
| 4 | 5 | Toluene | 1000 | MMAO | 2500 | ETY | 35 | 30 | 2.1 | 12 | 4800 | 566 | 205 | 2.77 |
| 5 | 5 | Toluene | 1000 | MMAO | 2500 | ETY | 50 | 30 | 2.1 | 10 | 4000 | 563 | 132 | 4.25 |
| 6 | 5.29 | Toluene | 1000 | MMAO | 1471 | ETY | 35 | 30 | 2.1 | 15 | 5671 | 400 | 140 | 2.86 |
| 7 | 10 | Toluene | 1000 | MMAO | 500 | ETY | 35 | 30 | 3.0 | 29 | 5800 | 464 | 186 | 2.50 |
| 8 | 10 | Hexanes | 1000 | MMAO | 500 | ETY | 35 | 30 | 2.1 | 16 | 3200 | 500 | 175 | 2.86 |
| 10 | 10 | Toluene | 1000 | MMAO | 500 | ETY | 50 | 10 | 3.0 | 24 | 14400 | 424 | 183 | 2.31 |
| 11 | 5 | Toluene | 1000 | MMAO | 500 | ETY | 75 | 30 | 2.1 | 11 | 4400 | 249 | 183 | 2.62 |
| 13 | 10 | Toluene | 1000 | MMAO | 500 | ETY | 50 | 30 | 3.0 | 30 | 6000 | 451 | 171 | 2.64 |
| 17 | 5 | Toluene | 1000 | MMAO | 500 | ETY | 50 | 30 | 3.0 | 19 | 22800 | - | - | - |

$a$. Activity = (kg P / mol Ni hr)

FIG. 4

Copolymerization of ethylene and acrylates

| Reaction | Cat. total (μmoL) | Solvent | Vol (mL) | Cocat. | Eq. | Mon. | T (°C) | Time (min) | P (MPag) | Yield (g) | Activity[a] | $M_w$ (x$10^3$) | $M_n$ (x$10^3$) | PDI |
|---|---|---|---|---|---|---|---|---|---|---|---|---|---|---|
| 14 | 68.5 | Toluene | 500 | MMAO | 500 | ETY-co-MA | 50 | 60 | 3.0 | 5 | 73 | 203 | 38 | 5.32 |
| 15 | 50 | Toluene | 500 | MMAO | 500 | ETY-co-tBA | 50 | 60 | 3.0 | 1 | 20 | 356 | 74 | 4.80 | a. Activity = (kg P / mol Ni hr)

FIG. 5

Copolymerization of ethylene and 1-hexene

| Reaction | Cat. total (μmoL) | Solvent | Vol (mL) | Cocat. | Eq. | Mon. | T (°C) | Time (min) | P (MPag) | Yield | Activity[a] | $M_w$ (x$10^3$) | $M_n$ (x$10^3$) | PDI |
|---|---|---|---|---|---|---|---|---|---|---|---|---|---|---|
| 16 | 25 | Toluene | 450 | MMAO | 500 | 1-hexene | - | 2 | 3.0 | 30 | 28800 | 287 | 33 | 8.87 |
| 18 | 5 | Toluene | 450 | MMAO | 500 | 1-hexene | 50 | 10 | 3.0 | 13 | 15600 | - | - | - | a. Activity = (kg P / mol Ni hr)

FIG. 6

TRANSITION METAL INITIATORS SUPPORTED BY KETONE DIIMINE LIGANDS FOR THE HOMOPOLYMERIZATION OF OLEFINS AND THE COPOLYMERIZATION OF OLEFINS WITH POLAR COMONOMERS

CROSS-REFERENCE TO RELATED APPLICATIONS

This application claims the benefit of Provisional Patent Application No. 61/128,174, filed on May 19, 2008, which is incorporated by reference herein.

BACKGROUND

1. Field of the Invention

The present invention relates generally to polymers, and more particularly to organometallic initiators capable of polymerizing and copolymerizing olefins.

2. Related Art

Interest in metal-mediated polymerization of olefins remains unabated in academic and industrial laboratories. Recent advances in stereo control and improved functionality tolerance, together with insight from mechanistic and theoretical studies, have considerably improved control over the final polymer structures and thereby the bulk properties of the resulting materials (1, 2, 3, 4, 5, 6, 7).

Tailoring of the bulk properties of polyolefins by synthetic control is still a major focus of many industrial and academic research groups. These efforts have produced a progression in catalysts design, from heterogeneous catalysts to "single-site" systems whose reactivity can be fine tuned by choice of the ligand environment surrounding the active metal center (1, 2, 3, 4, 5, 6, 7). Novel structures based on electrophilic early transition metal based catalysts, together with advances in the activation by co-catalysts and improved mechanistic understanding, have played a significant role in this development. Examples of how the metal center can tailor properties by controlling monomer insertion include the stereo specific polymerization of propene (8, 9, 10, 11, 12, 13, 14) and the copolymerization of ethylene and 1-alkenes (15, 16, 17, 18).

Recently the design of late transition metal initiators has received renewed interest because of their lower oxophilicity and resistance toward deactivation by polar functionalities, relative to their early transition metal counterparts (19, 20, 21, 22, 23). This reduced sensitivity of late metals to polar impurities allows for polymerizations to be carried out under less stringent conditions and allows for the copolymerization with polar comonomers (24, 25, 26, 27, 28). Nickel and palladium based catalysts have been shown to participate in chain walking reactions (29, 30, 31), tolerate polar functionalities (24, 25, 26, 27, 28) and have even been used in water (32, 33, 34). These catalytic properties are of significant interest for developing materials with unique properties and for the development of new commercial processes.

The introduction of cationic Pd(II) and Ni(II)-based catalysts which convert ethylene and α-olefins to high molar mass polymers, by Brookhart et al., rejuvenated the area of ethylene polymerization with late metal catalysts (1, 2, 3, 4, 5, 6, 7, 19, 20). The highly electrophilic metal center, and steric bulk on the ligand are important features for the generation of high molecular weight polymer. The electrophilicity of the late metal center results in rapid rates of olefin insertion while the use of bulk favors insertion over chain transfer. The variation of the backbone and aryl substituents, on the ligand, allow for further control over steric and electronic effects at the metal center (1, 2, 3, 4, 5, 6, 7, 46).

Copper(II) and zinc(II) complexes supported by a β-diimine ligand, undergo oxidative degradation to give a ketone diimine derivative under aerobic conditions (Yokota et al.) (44).

Recent literature shows current interest in the transition metal mediated living polymerization of olefins. These reactions allow for the synthesis of polyolefins with higher order architectures and improved physical properties (47, 48). In contrast to early transition metal catalysts, late metal systems are more tolerant toward functionality (49, 20, 21, 50) and participate in "chain-walking" reactions (3, 30, 51, 52, 53) in which the metal center migrates along the growing polymer chain through a series of β-hydride elimination and reinsertion steps. The polymerization of ethylene by late metal cationic systems results in polyethylene (PE) with various degrees of branching. Similarly, "ethylene" sequences (18, 54) can be generated from the chain straightening of higher α-olefins (3, 30, 51, 52, 53). These distinctive features in combination with living behavior, have led to the generation of novel materials such as elastomeric multi-block poly(α-olefins) (54), ethylene-propylene type copolymers (18), regioblock copolymers (18, 55, 56), and end-functionalized amorphous PE (24).

SUMMARY

Currently, there is an absence of late metal systems capable of producing semicrystalline PE directly from ethylene under living conditions. Therefore, a novel ligand metal combination, or initiator, is provided. Upon activation with various co-catalysts, the initiator polymerizes ethylene and propylene, and/or other olefin monomers, to high molecular weight polymers. Additionally, the copolymerization of olefins with functionalized comonomers can be carried out. In some embodiments, polymerization can be carried out in a living manner.

The general initiator structure comprises a late transition metal with a neutral chelating ligand that contains a Lewis basic functionality.

In one aspect, the general initiator structure comprises the following formula (I):

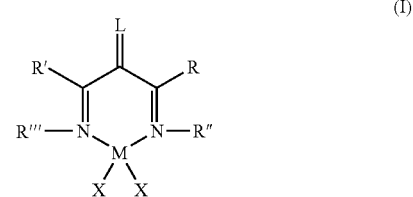

wherein:

R, R', R" and R'" are each independently an achiral or chiral alkyl or aryl group with or without one or more functional groups;

M is Fe, Co, Ni, Pd or Pt;

X is an alkyl, hydride or halide group; and

L is O, N—R"", S, or =CH$_2$, wherein R"" is an alkyl or aryl group.

Various embodiments are provided, including embodiments in which R and R' are each alkyl, and R" and R'" are each aryl; embodiments in which L is O; embodiments in which L is O, R and R' are each alkyl, and R" and R'" are each aryl; embodiments in which R and R' are each methyl, and R" and R'" are each aryl, including embodiments where L is O; embodiments in which R and R' are each alkyl, and R" and R'" are each 2,6 disubstituted aryl, including embodiments where L is O; and embodiments in which the initiator is 2,4-bis(2,6-diisopropylphenylimino)pentan-3-one nickel dibromide, or 2,4-bis(2-isopropyl-6-methylphenylimino)pentan-3-one nickel dibromide.

In another aspect, a process of producing an organometallic initiator complex is provided, comprising mixing a metal compound with a ligand of the following formula (II)

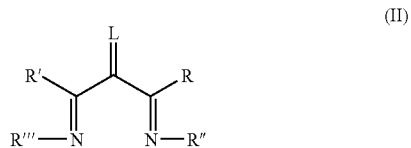

(II)

wherein R, R', R" and R'" are each independently an achiral or chiral alkyl or aryl group with or without one or more functional groups, and L is O, N—R"", S, or =CH$_2$, wherein R"" is an alkyl or aryl group.

Various embodiments are provided, including embodiments in which R and R' are each alkyl, and R" and R'" are each aryl; embodiments in which L is O; embodiments in which L is O, R and R' are each alkyl, and R" and R'" are each aryl; embodiments in which R and R' are each methyl, and R" and R'" are each aryl, including embodiments where L is O; embodiments in which R and R' are each alkyl, and R" and R'" are each 2,6 disubstituted aryl, including embodiments where L is O; and embodiments in which R" and R'" are each 2,6-diisopropylphenyl or 2-isopropyl-6-methylphenyl.

In some embodiments, the process producing an organometallic complex utilizes a metal halide complex as the metal compound, which in certain embodiments is a (1,2-dimethoxyethane)NiBr$_2$ complex.

In a further aspect, a polymerization process is provided. The process comprises mixing one, or more than one, olefin with an organometallic complex so as to produce a polymer that comprises the one, or more than one, olefin. In this process, the organometallic complex has the structure of formula (I), or any embodiments of formula (I). Various embodiments are provided, including embodiments in which R and R' are each alkyl, and R" and R'" are each aryl; embodiments in which L is O; embodiments in which L is O, R and R' are each alkyl, and R" and R'" are each aryl; embodiments in which R and R' are each methyl, and R" and R'" are each aryl, including embodiments where L is O; embodiments in which R and R' are each alkyl, and R" and R'" are each 2,6 disubstituted aryl, including embodiments where L is O; and embodiments in which the organometallic complex is 2,4-bis(2,6-diisopropylphenylimino)pentan-3-one nickel dibromide, or 2,4-bis(2-isopropyl-6-methylphenylimino)pentan-3-one nickel dibromide.

In various embodiments, the polymerization process utilizes one or more olefins that are each independently: R$^1$CH=CH$_2$; cyclopentene; styrene; norbornene; cyclopentene, styrene, or norbornene substituted with one or more functional groups; or a polar olefin of the formula H$_2$C=CR$^2$X; where R$^1$ is either hydrogen, an alkyl group, or an alkyl group substituted with one or more functional groups, R$^2$ is hydrogen, an alkyl group, an aryl group or an alkoxy group, and X is a polar group. Examples of X include, but are not limited to: a halogen such as Cl, Br, or F; —CN; —C$_6$H$_5$N; —CONR$^3$R$^4$; —OR$^3$; —COOR$^3$; —OCOR$^3$; —COR$^3$; —C$_6$H$_5$ OR$^3$; and/or —C$_6$H$_5$NR$^3$R$^4$; wherein R$^3$ and R$^4$ are each independently hydrogen or an alkyl group, which can be a C$_{1-12}$ alkyl group.

In particular embodiments, the polar olefin can be H$_2$C=CH(CH$_2$)$_n$CO$_2$R$^5$, where R$^5$ is hydrogen or an alkyl group, and n is between 0 and 20.

In some embodiments, the polymerization process utilizes a single olefin, such as any one of the olefins described herein, resulting in homopolymerization. In other embodiments, the polymerization process utilizes two or more than two different olefins, which can include at least one or any combination of the olefins described herein, resulting in copolymerization.

The polymerization process can be carried out under living polymerization conditions such that a polymer is produced by a living polymerization process. In such embodiments, the use of two, three or more than three different monomers, which can include at least one or any combination of the olefins described herein, can produce a block copolymer.

In yet another aspect of the above polymerization processes, a co-catalyst is used. The co-catalyst can be added to any embodiment of the polymerization process, and can be an alkylaluminum, aluminoxane, or borate compound.

In various embodiments, the polymerization products produced by the polymerization process include semicrystalline polymers.

BRIEF DESCRIPTION OF THE DRAWINGS

For a more complete understanding of the present invention, reference is now made to the following descriptions taken in conjunction with the accompanying drawings, in which.

FIG. 4 is a table illustrating the larger scale polymerization of ethylene with initiator 1;

FIG. 5 is a table illustrating the larger scale copolymerization of ethylene and acrylates with initiator 1;

FIG. 6 is a table illustrating the larger scale copolymerization of ethylene and 1-hexene;

DETAILED DESCRIPTION

Figure 1:
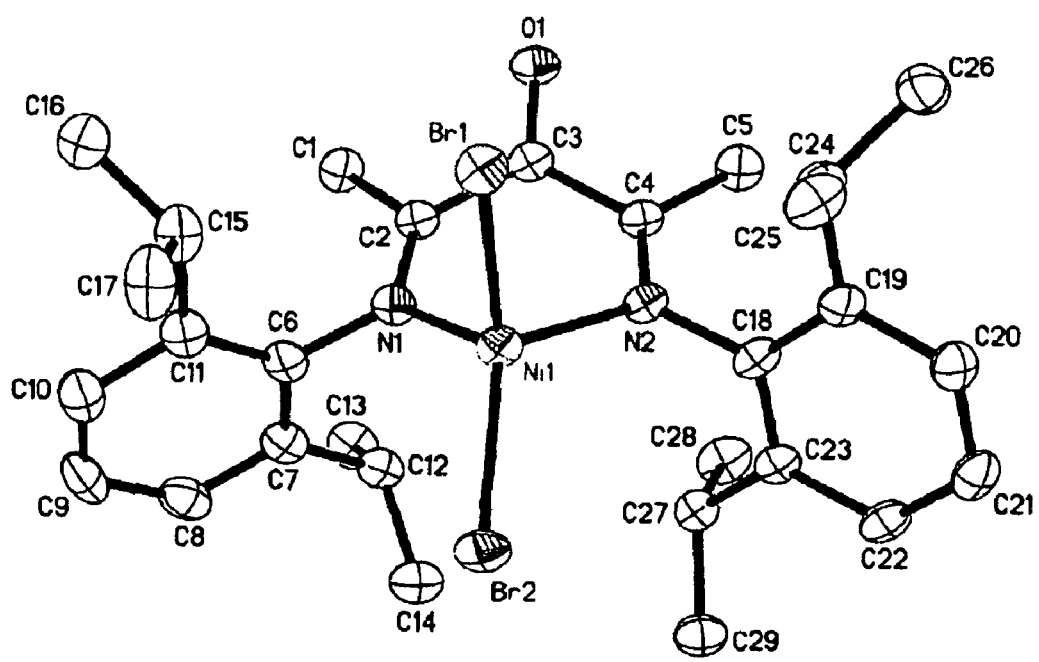
FIG. 1 is an ORTEP drawing of initiator 1 at the 50% probability level.

Novel organometallic initiator complexes are provided that are capable of polymerizing olefins or copolymerizing olefins with functionalized comonomers to yield high molecular weight polymers (≧5,000).

More particularly, these initiator complexes have the following formula (I):

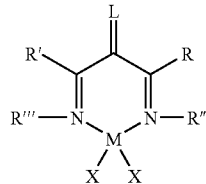

(I)

where R, R', R" and R'" are each independently an achiral or chiral alkyl or aryl group with or without one or more functional groups; M is Fe, Co, Ni or Pd; X is an alkyl, hydride or halide group; and L is O, N—R"", S, or =CH$_2$, where R"" is an alkyl or aryl group. In particular embodiments, the initiator is 2,4-bis(2,6-diisopropylphenylimino)pentan-3-one nickel dibromide or 2,4-bis(2-isopropyl-6-methylphenylimino)pentan-3-one nickel dibromide.

The term "alkyl" refers to a branched or unbranched saturated hydrocarbyl group such as methyl, ethyl, n-propyl, isopropyl, n-butyl, isobutyl, t-butyl, octyl, decyl, and the like, as well as cycloalkyl groups such as cyclopentyl, cyclohexyl and the like. In particular embodiments, an alkyl group can be C$_{1-30}$ or C$_{1-20}$.

The term "aryl" refers to an aromatic hydrocarbyl group containing a single aromatic ring or multiple aromatic rings that are fused together, linked covalently, or linked to a common group such as a methylene or ethylene moiety. In some embodiments, aryl groups contain one aromatic ring or two fused or linked aromatic rings, e.g., phenyl, naphthyl, biphenyl, diphenylether, diphenylamine, benzophenone, and the like. In particular embodiments, an aryl group including any substituents can have from 4 to 50 carbon atoms, 4 to 40 carbon atoms, 4 to 30 carbon atoms, 4 to 20 carbon atoms, or 4 to 10 carbon atoms, or more particularly, can have from 6 to 50 carbon atoms, 6 to 40 carbon atoms, 6 to 30 carbon atoms, 6 to 20 carbon atoms or 6 to 10 carbon atoms.

The term "alkoxy" refers to an alkyl group bound through a single, terminal ether linkage; that is, an alkoxy group may be represented as —O-alkyl, where alkyl is as defined above.

An alkyl group or an aryl group can be substituted with a functional group. As used herein, the term "substituted" in connection with a hydrocarbyl group refers to a hydrocarbyl group in which at least one hydrogen atom bound to a carbon atom is replaced with one or more substituents. For example, a disubstituted aryl group, such as a diisopropylphenyl group, has two substituents replacing two hydrogen atoms of the parent aryl group. A substituent can be a "functionality" or "functional group" such as, but not limited to, halo, ester, keto (oxo), amino, imino, hydroxyl, carboxyl, phosphite, phosphonite, phosphine, phosphinite, thioether, amide, nitrile, and ether. For example, methyl acrylate can be considered a hydrocarbyl substituted with a carboxyl functional group. In particular embodiments, an alkyl or aryl group can have one, two, three, four, or more than four, substituents.

In the complex of formula (I), R, R', R" and R'" can each independently be an achiral or chiral hydrocarbyl group. As is known, the term "chiral" refers to molecules which have the property of non-superimposability on their mirror image partner, while the term "achiral" refers to molecules which are superimposable on their mirror image partner.

Initiators can be prepared by combining a ligand with an appropriate metal. In some embodiments, the initiators are prepared via a reaction sequence, as shown in Example 1 (below). A general formula (II) of such a ligand is as follows:

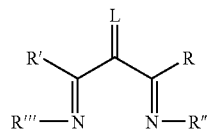

(II)

where R, R', R" and R'" are each independently an achiral or chiral alkyl or aryl group with or without one or more functional groups, and L is O, N—R"", S, or =CH$_2$, with R"" being an alkyl or aryl group.

Initiators of the present invention can polymerize and/or copolymerize one or more of the following olefins: R$^1$CH=CH$_2$, cyclopentene, styrene, norbornene; substituted cyclopentene, styrene or norbornene derivatives bearing one or more functional groups; or a polar olefin of the formula H$_2$C=CR$^2$X; where R$^1$ is either hydrogen, an alkyl group, or an alkyl group substituted with one or more functional groups, R$^2$ is hydrogen, an alkyl group, an aryl group or an alkoxy group, and X is a polar group. In these embodiments, R$^1$ can be hydrogen, alkyl, or a substituted alkyl bearing one or more functional groups (such as, —OH, —NH$_2$, CN, —COOR, —OCOR, —C(O)R, or —C(O)NRR', where R and R' are each independently hydrogen or an alkyl group). Examples of X include, but are not limited to: a halogen such as Cl, Br, or F; —CN; —C$_6$H$_5$N; —CONR$^3$R$^4$; —OR$^3$; —COOR$^3$; —OCOR$^3$; —C$_6$H$_5$OR$^3$; —COR$^3$ and/or —C$_6$H$_5$NR$^3$R$^4$; wherein R$^3$ and R$^4$ are each independently hydrogen or an alkyl group, which can be a C$_{1-12}$ alkyl group. Additionally, the polar olefin can be H$_2$C=CH(CH$_2$)$_n$CO$_2$R$^5$, where R$^5$ is hydrogen or an alkyl group, and n is between 0 and 20. Polymers generated in connection with these initiators can exhibit a unique microstructure.

Polymerizations can occur at temperatures from at or about −100° C. to at or about 250° C. The preferred range is at or about 60° C. to at or about 200° C. Using such polymerizations conditions, with ethylene or propylene, high molecular weight polymers with a unique architecture can be produced (as in Examples 2 and 3, below). In another embodiment, these initiators can be used for copolymerization of ethylene with functionalized comonomers (as in Example 4, below) or other 1-alkenes.

Co-catalysts can be used with the above initiators for polymerization/copolymerization reactions. Such co-catalysts include, but are not limited to, any alkylaluminum, alkylaluminoxane, and borate co-catalyst known in the art. Such co-catalysts include, but are not limited to, methylaluminoxane (MAO), modified methylaluminoxane type-3A, or trimethylaluminum (TMA).

In certain embodiments with the initiator complex of formula (I), polymerization can occur under conditions that result in a living polymerization process. In these embodiments, a single monomer can be polymerized in a living manner, or more than one monomer can undergo living polymerization. By adjusting conditions such as temperature and pressure, living polymerization can occur so that the growth of M$_n$ of the polymer as a function of time is linear. Under living conditions, molecular weight distributions that are symmetric and polymers with PDI values of less than or equal to 1.3 can be obtained.

Using living conditions, block copolymers, including diblock, triblock and other multiblock copolymers, can be prepared. For example, under living polymerization conditions, a first monomer can be polymerized to produce a polymer product, and then a second monomer can be added to the polymer product to produce a block copolymer. In addition, tapered, regioblock and/or end functionalized polymers can be prepared.

Polymerization under living conditions can also yield semicrystalline polymers such as semicrystalline polyethylene or polypropylene. The term "semicrystalline" refers to polymers that have both a crystalline portion and an amorphous portion. Polymerization under living conditions can also yield amorphous polymers.

The present invention may be better understood by referring to the accompanying examples, which are intended for illustration purposes only and should not in any sense be construed as limiting the scope of the invention as defined in the claims appended hereto.

EXAMPLE 1

Synthesis of Initiator 1

2,4-bis(2,6-diisopropylphenylimino)pentan-3-one nickel dibromide (initiator 1)

Initiator 1 is synthesized from the ligand, 2,4-bis(2,6-diisopropylphenylimino)pentan-3-one. This ligand can be made according the following scheme and procedure.

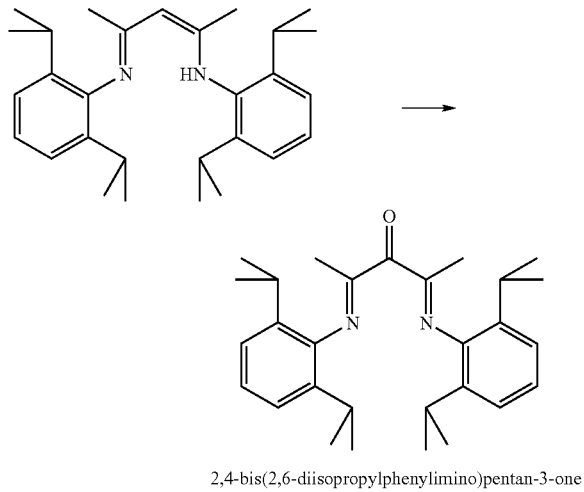

2,4-bis(2,6-diisopropylphenylimino)pentan-3-one

[$Cu^{II}$(1)(AcO)]. To a solution of $Cu^{II}(CH_3COO)_2$—$H_2O$ (2.38 g) in $CH_3OH$—$CH_2Cl_2$ (v/v=1:1,500 mL) was added drop-wise a solution of 1 (5 g) in $CH_2Cl_2$ (20 mL) while stirring at room temperature. After stirring the mixture overnight, the solvent was removed in vacuo. The resulting brown material was dissolved in $CH_2Cl_2$ (100 ml) and extracted with water three times (100 mL×3). The solvent was removed in-vacuo and the brown solid was washed with water and collected by filtration onto a fritted funnel and dried under high vacuum overnight (5.5 g, 84.9%).

[$Cu^{II}$(1)AcO] (5 g) was treated in methanol (1000 mL) at 50° C. in a 3 neck round bottom flask capped with two septa and a reflux condenser attached to an oil bubbler. Oxygen was vigorously bubbled through the solution for 72 hours or until a complete color change from brown to purple was noted. At this point oxygen was bubbled through for another 12 hours and the volume was reduced to 100 mL by bubbling oxygen through at 50° C. The methanol solution was cooled by allowing to stand at room temperature, overnight, under an atmosphere of oxygen. Purple crystals were collected by filtration. 2,4-bis(2,6-diisopropylphenylimino)pentan-3-one (3 g, 75.2%) was isolated by treating the purple crystals with aqueous $NH_3$. Removal of the solvent gave a pale yellow solid.

The synthesis of initiator 1 was carried out under an inert atmosphere according to Scheme 1. All reagents were dried, by various methods, prior to use. To a stirring suspension of (1,2-dimethoxyethane)$NiBr_2$ complex (71. 1 mg, 0.231 mmol) in 15 mL methylene chloride, 2,4-bis(2,6-diisopropylphenylimino)pentan-3-one (100 mg, 0.231 mmol), in 5 ml methylene chloride, was added at once, at room temperature. Shortly after the addition of the ligand, the solution began to turn red. The suspension was allowed to stir for an additional 2.5 hours at room temperature. The reaction mixture was then filtered through celite and the solvent removed in-vacuo. The corresponding red powder was washed with cold diethyl ether (−35° C., 3×, 10 mL), dried, resuspended in methylene chloride (10 mL), refiltered through celite and then dried to give the pure compound as a red powder in 49.0% yield (73.7 mg, 0.113 mmol). Anal. Calc. ($C_{29}H_{40}N_2$) C, 53.49; H, 6.19; N, 4.30. Found: C, 53.71; H, 6.24; N, 4.23.

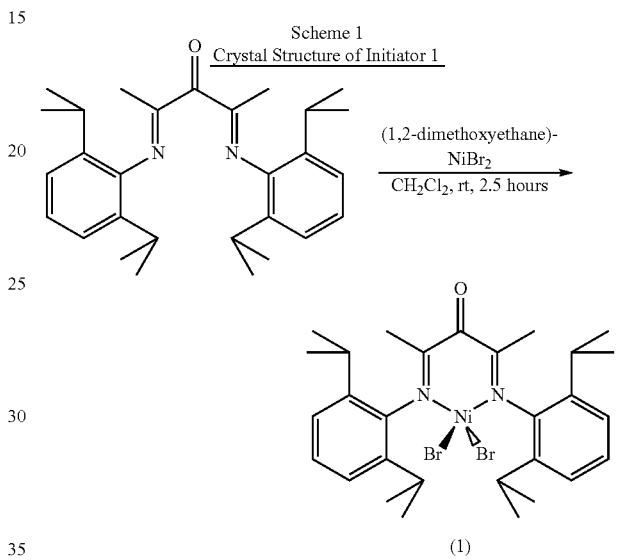

Scheme 1
Crystal Structure of Initiator 1

Single crystals were obtained from a concentrated solution in methylene chloride at −35° C. The molecular connectivity is consistent with an N,N-coordinated structure in which the ligand is bound as a neutral donor. Bond distances within the six membered chelate ring are consistent with the structure drawn in Scheme 1 as illustrated by the following selected bond lengths (Å): C(4)-N(2) 1.291, C(3)-C(4) 1.518, C(2)-N (1) 1.288, C(2)-C(3) 1.511 and C(3)-O(1) 1.222. The Ni(II) atom adopts a pseudotetrahedral coordination geometry with a contact shifted $^1$H-NMR exhibiting relatively narrow line widths at room temperature. The six membered chelate ring adopts a boat conformation. See FIG. 1 for the ORTEP drawing of Initiator 1.

EXAMPLE 2

Polymerization of Ethylene

Figure 3:
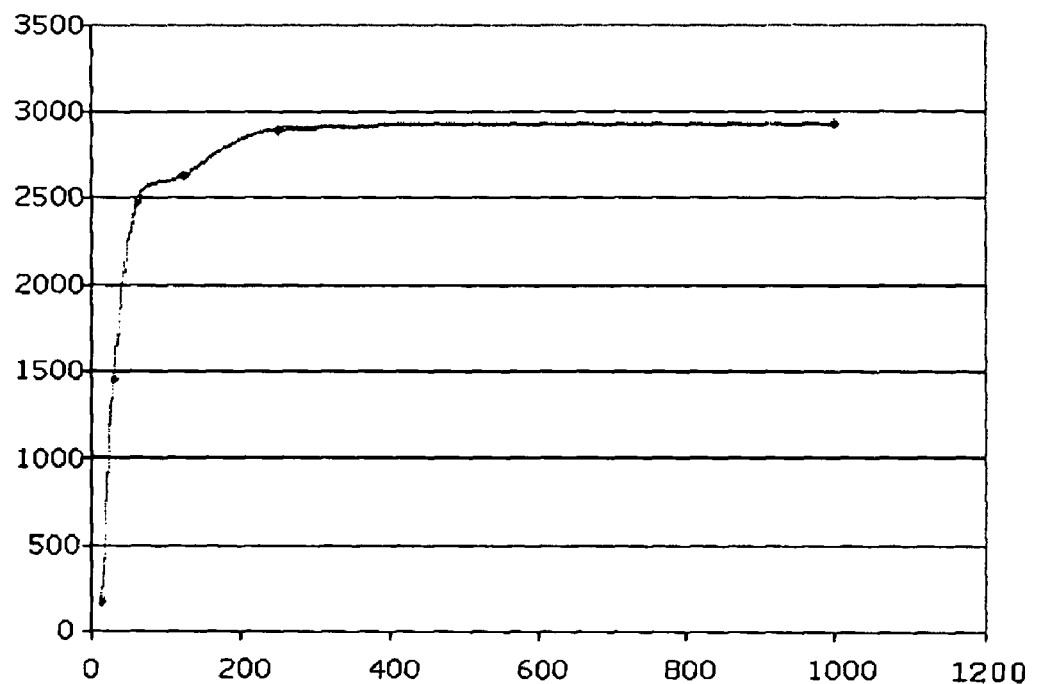
FIG. 3 is a graph showing optimization of cocatalyst with the initiator in polymerization experiments.

Homopolymerizations of ethylene were conducted in the following manner using initiator 1. A 300 mL steel autoclave reactor, equipped with an addition funnel was loaded, inside a glovebox with initiator 1 in 90 mL of toluene. Methylaluminoxane (Aldrich, 10 wt. % in toluene) (MAO) was added to the addition funnel followed by toluene so that the final volume was 10 mL. The reactor was sealed inside the glovebox and attached to an ethylene line. The reactor was pre-pressurized with ethylene. The MAO solution was then injected under a specified pressure of ethylene, which was fed continuously at that pressure over the course of the reaction. Ethylene was vented after a specified amount of time and acidified methanol (10% HCl) was added to quench the polymerization. The precipitated polymer was collected by filtration, washed copiously with methanol, followed by acetone and dried under high vacuum overnight. Polymerization activities were calculated from the mass of the product obtained. Polymers were characterized by GPC analysis, relative to polystyrene standards, at 135° C. in o-dichlorobenzene (in a Polymer Laboratories, high-temperature chromatograph, Pl-GPC 200). Polymer melting points were measured on a TA instruments differential scanning calorimeter, (model DSC 2920) at a rate of 10° C./min for three cycles using a temperature range of 0-180° C. The optimal amount of cocatalyst (MAO) was determined as shown in FIG. 3. Table 1 shows selected polymerization data.

TABLE 1

Selected Ethylene Homopolymerization Reactions

| Conc [μmol] | Cocatalyst [eq. MAO] | Ethylene [psi] | Temp. [° C.] | Activity[a] | $M_n \times 10^4$ | $M_w \times 10^4$ | PDI | $T_m$ [° C.] |
|---|---|---|---|---|---|---|---|---|
| 5 | 250 | 300 | 32.5 | 2787 | 131 | 177 | 1.36 | 113.7 |
| 5 | 250 | 300 | 20.0 | 1576 | 58.7 | 66.3 | 1.13 | — |
| 5 | 1000 | 300 | 30 | 2800 | 119 | 144 | 1.20 | — |
| 2.5 | 250 | 300 | 30→40 | 4500 | 98 | 140 | 1.50 | — |

[a] Activity = (kg P/mol Ni hr)

Table 1 illustrates the relationship between temperature and activity. The activity increases dramatically with temperature, however, only mass transfer limited rates could be obtained above 40° C. The polymer produced exhibits high molecular weights (>1×10$^6$) with relatively short reaction times (ca. 10 min). The polymers produced have melting points between 80 and 125° C.

EXAMPLE 3

Polymerization of Propene

Homopolymerizations of propene were conducted in the following manner using initiator 1. A 300 mL steel autoclave reactor, equipped with an addition funnel was loaded, inside a glovebox with initiator 1 in 90 mL of toluene. MAO (Aldrich, 10 wt. % in toluene) was added to the addition funnel followed by toluene so that the final volume was 10 mL. The reactor was sealed inside the glovebox and attached to a propene line. The reactor was pre-pressurized with propene. The MAO solution was then injected under a specified pressure of propene, which was fed continuously at that pressure over the course of the reaction. Ethylene was vented after a specified amount of time and acidified methanol (10% HCl) was added to quench the polymerization. The precipitated polymer was collected by filtration, washed copiously with methanol, followed by acetone and dried under high vacuum overnight. Polymerization activities were calculated from the mass of the product obtained. Polymers were characterized by GPC analysis, relative to polystyrene standards, at 135° C. in o-dichlorobenzene (in a Polymer Laboratories, high-temperature chromatograph, Pl-GPC 200). Glass transitions ($T_g$) and melting temperatures ($T_m$) were measured on a TA instruments differential scanning calorimeter, (model DSC 2920) at a rate of 5° C./min for three cycles using a temperature range of −70-180° C. $^{13}$C NMR spectra of the polymers was obtained in 1,1,2,2-tetrachloroethane-d$_2$ at room temperature. Table 2 (below) shows selected polymerization data.

TABLE 2

Selected Propene Homopolymerization Reactions

| | Conc [μmol] | Cocatalyst [eq. MAO] | Propene [psi] | Temp. [° C.] | Activity[a] | $M_n \times 10^3$ | $M_w \times 10^3$ | PDI | $T_g$ [° C.] |
|---|---|---|---|---|---|---|---|---|---|
| 1 | 30 | 250 | 150 | 0 | 6.1 | 138 | 155 | 1.13 | −23 |
| 2 | 30 | 250 | 150 | 25 | 75 | 316 | 469 | 1.49 | −25 |
| 3 | 5 | 250 | 150 | 35 | 98 | 113 | 229 | 2.04 | — |
| 4 | 30 | 250 | 150 | 50 | 33 | 191 | 403 | 2.11 | −32 |

[a] Activity = (kg P/mol Ni hr)

The polypropylene produced is mainly amorphous with $T_g$s ranging from −35° C. to −20° C. depending on the reaction temperature. Entry 1, 2 and 4 exhibit the following tacticity as illustrated in Table 3, below.

TABLE 3

Tacticity of Polypropylene obtained with initiator 1

| | mm (%) | mr (%) | rr (%) |
|---|---|---|---|
| 1 | 18.9 | 34.9 | 46.3 |
| 2 | 37.2 | 33.9 | 28.9 |
| 4 | 16.0 | 34.4 | 49.6 |

The inherent differences in the microstructure of the polypropylene produced at different temperatures illustrates that these catalysts allow for microstructure control in the final product through variations in temperature, pressure, monomer concentration and other various reaction conditions. Additionally variations in the ligand are expected to give further control and substantial stereoregularity. The presence of a melting point $T_m$=150° C. and $T_c$=117° C. in Entry 3 illustrates that polypropylene obtained with initiator 1 exhibits some crystallinity.

EXAMPLE 4

Copolymerization of Ethylene and Methyl Acrylate

Copolymerizations of ethylene and methyl acrylate were conducted in the following manner using initiator 1. A 300 mL steel autoclave reactor, equipped with an addition funnel was loaded, inside a glovebox with initiator 1 in 90 mL of toluene. MAO (Aldrich, 10 wt. % in toluene) was added to the addition funnel along with a specified amount of neat methyl acrylate, followed by toluene so that the final volume was 10 mL. The reactor was sealed inside the glovebox and attached to an ethylene line. The reactor was pre-pressurized with ethylene. The MAO-methyl acrylate solution was then injected under a specified pressure of ethylene, which was fed continuously at that pressure over the course of the reaction. Ethylene was vented after a specified amount of time and acidified methanol (10% HCl) was added to quench the polymerization. The precipitated polymer was collected by centrifugation, washed copiously with methanol, followed by THF, and dried under high vacuum overnight. Polymerization activities were calculated from the mass of the product obtained. Polymers were characterized by GPC analysis, relative to polystyrene standards, at 135° C. in o-dichlorobenzene (in a Polymer Laboratories, high-temperature chromatograph, Pl-GPC 200). $^1$H NMR spectra of the polymers was obtained in 1,1,2,2-tetrachloroethane-$d_2$ at 115° C.

TABLE 4

Selected Ethylene-Methyl Acrylate Copolymerization Reactions

| Conc [µmol] | Cocatalyst [eq. MAO] | Ethylene [psi] | Temp. [° C.] | [MA] | Activity$^a$ | $M_n \times 10^3$ | $M_w \times 10^3$ | PDI | % Inc. |
|---|---|---|---|---|---|---|---|---|---|
| 20 | 1000 | 300 | 20 | 0.06 | 32 | 102 | 304 | 3.00 | ND |
| 10 | 1000 | 100 | 35 | 0.12 | 7.5 | 4.42 | 17.9 | 4.05 | 0.8 |

$^a$Activity = (kg P/mol Ni hr)

Figure 2:
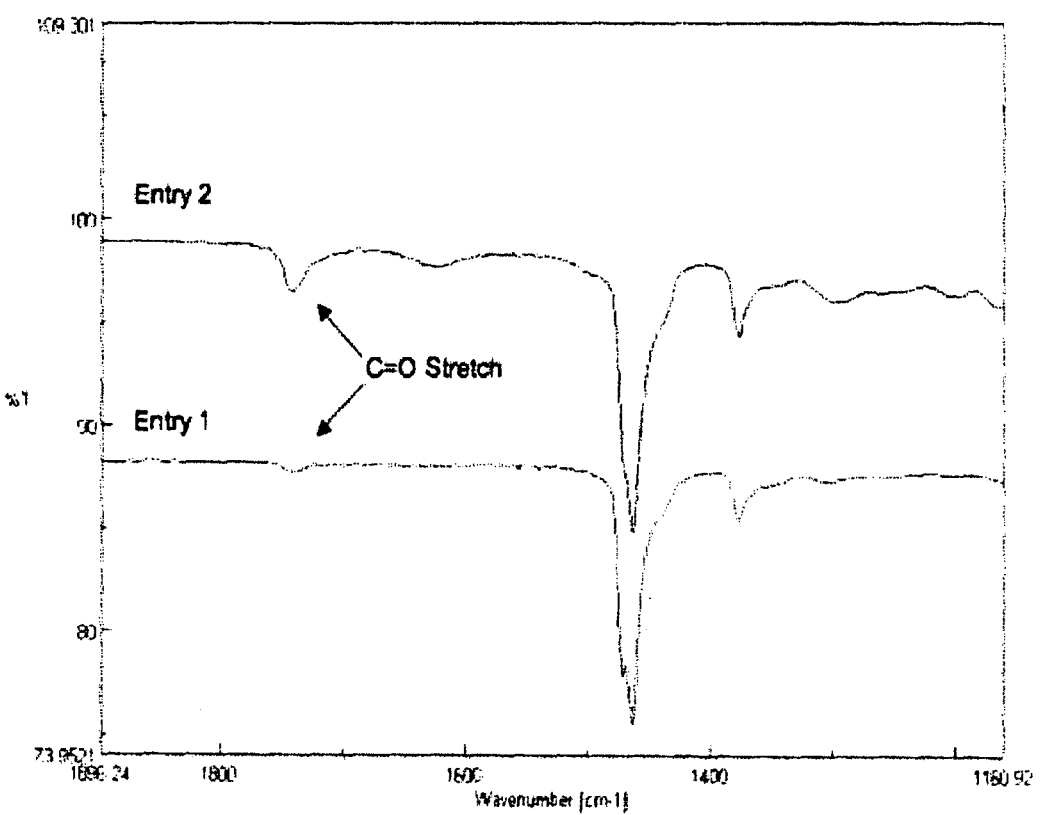
FIG. 2 is a graph of the IR spectras of copolymers showing incorporation of methyl acrylate into polyethylene.

Addition of methyl acrylate to the reaction resulted in significantly lowered activities, however, random copolymers with low levels of incorporation were generated. Better control over the final product through variations in reaction conditions and initiator structure are expected to improve the yield, activity, control and incorporation. Entry 1, Table 4, exhibits a characteristic (C=O) stretch in the IR spectrum, however, the incorporation is not detectable by $^1$H-NMR. At reduced ethylene pressures and elevated methyl acrylate concentrations, the incorporation is higher (Entry 2). FIG. 2, shows the IR spectra for Entry 1 and 2.

EXAMPLE 5

Larger Scale Polymerization of Ethylene with Initiator 1

Homopolymerizations of ethylene were conducted in the following manner using initiator 1. A 2000 mL steel autoclave reactor, equipped with an addition straw was heated in an oven at 150° C. overnight. The reactor was assembled, while hot and purged with nitrogen and pumped down a total of three times. The reactor was then sealed under nitrogen. A specified amount of solvent and co-catalyst were added using standard Schlenk and air-free techniques. A stock solution of the initiator was prepared and added to the addition straw under a stream of nitrogen. The reactor was sealed and attached to an ethylene line. The reactor was pre-pressurized with ethylene. The initiator solution was then injected under a specified pressure of ethylene, which was fed continuously at that pressure over the course of the reaction. 10 mL ethanol was added to quench the polymerization. The precipitated polymer was collected by filtration, washed copiously with acidified methanol (10% HCl); then washed with methanol followed by acetone and dried in a vacuum oven overnight. Polymerization activities were calculated from the mass of the product obtained. Polymers were characterized by GPC analysis, relative to polystyrene standards, at 135° C. in o-dichlorobenzene (in a Polymer Laboratories, high-temperature chromatograph, Pl-GPC 200). Polymer melting points were measured on a TA instruments differential scanning calorimeter, (model DSC 2920) at a rate of 10° C./min for three cycles using a temperature range of 0-180° C.

FIG. 4 shows selected polymerization data obtained from the homopolymerization of ethylene, and illustrates the following. The ethylene consumption is consistent over the course of 30 minutes. The activity is significantly higher when MMAO-3A is used as a co-catalyst versus MAO.

The activity increases significantly with temperature; up to 22800 kg P/mol Ni hr at 50° C. (reaction 17). Ethylene consumption is consistent for 30 minutes at 75° C. (reaction 11) illustrating the catalytic species is robust toward decomposition at elevated temperatures. Additionally, the catalytic species is highly active in the presence of $H_2$ (reaction 13). Melt flow rates of the polymer obtained in reaction 13 also suggest that $H_2$ acts as a chain transfer agent.

EXAMPLE 6

Larger Scale Copolymerization of Ethylene and Acrylates with Initiator (1)

Copolymerizations of ethylene and methyl or t-butyl acrylate were conducted in the following manner using initiator 1. A 2000 mL steel autoclave reactor, equipped with an addition straw was heated in an oven at 150° C. overnight. The reactor was assembled, while hot and purged with nitrogen and pumped down a total of three times. The reactor was then sealed under nitrogen. A specified amount of solvent, co-catalyst and acrylate were added using standard Schlenk and air-free techniques. Acrylate was added to give 0.082 M solution in reaction 14 and 15. A stock solution of the initiator was prepared and added to the addition straw. The reactor was sealed and attached to an ethylene line. The reactor was pre-pressurized with ethylene. The initiator solution was then injected under a specified pressure of ethylene, which was fed continuously at that pressure over the course of the reaction. 10 mL ethanol was added to quench the polymerization. The precipitated polymer was collected by filtration, washed copiously with acidified methanol (10% HCl); then washed with methanol followed by acetone and dried in a vacuum oven overnight. Polymerization activities were calculated from the mass of the product obtained. Polymers were characterized by GPC analysis, relative to polystyrene standards, at 135° C. in o-dichlorobenzene (in a Polymer Laboratories, high-temperature chromatograph, Pl-GPC 200). $^1$H and 13C NMR spectra of the polymers was obtained in 1,1,2,2-tetrachloroethane-$d_2$ at 115° C.

FIG. 5 shows the results of copolymerizations using ethylene and acrylates. The figure illustrates that the copolymerization of ethylene and methyl acrylate proceeds with good activity in the presence of MMAO at 50° C. and 3.0 MPag. The incorporation of methyl acrylate was 0.14 mol % in reaction 14. Compared to the smaller scale reactions this illustrates that the choice of co-catalyst and reaction conditions are important for activity, incorporation and polymer microstructure. Under the same conditions, the copolymerization of ethylene and tert-butyl acrylate showed lower activity and less incorporation. No incorporation was detectable by NMR for reaction 15, however, a peak corresponding to the (C=O) stretch was observed in the IR spectrum of the copolymer generated.

EXAMPLE 7

Larger Scale Copolymerization of Ethylene and 1-hexene with Initiator (1)

Copolymerizations of ethylene and 1-hexene were conducted in the following manner using initiator 1. A 2000 mL steel autoclave reactor, equipped with an addition straw was heated in an oven at 150° C. overnight. The reactor was assembled, while hot and purged with nitrogen and pumped down a total of three times. The reactor was then sealed under nitrogen. A specified amount of solvent, co-catalyst and 50 mL 1-hexene were added using standard Schlenk and air-free techniques. A stock solution of the initiator was prepared and added to the addition straw. The reactor was sealed and attached to an ethylene line. The reactor was pre-pressurized with ethylene. The initiator solution was then injected under a specified pressure of ethylene, which was fed continuously at that pressure over the course of the reaction. 10 mL ethanol was added to quench the polymerization. The precipitated polymer was collected by filtration, washed copiously with acidified methanol (10% HCl); then washed with methanol followed by acetone and dried in a vacuum oven overnight. Polymerization activities were calculated from the mass of the product obtained. Polymers were characterized by GPC analysis, relative to polystyrene standards, at 135° C. in o-dichlorobenzene (in a Polymer Laboratories, high-temperature chromatograph, Pl-GPC 200). $^1$H and $^{13}$C NMR spectra of the polymers was obtained in 1,1,2,2-tetrachloroethane-$d_2$ at 115

Results of the above copolymerization reactions of ethylene and 1-hexene are shown in FIG. 6. The figure illustrates that Reaction 16 showed a high activity, consistent with a rate increase in the copolymerization reaction. Although temperature control was not maintained, based on the presence of additional butyl and long chain branching the incorporation of 1-hexene was calculated to be 0.32 mol %. This illustrates that ethylene and 1-hexene can be copolymerized with high activities.

EXAMPLE 8

Synthesis of 2,4-bis(2-isopropyl-6-methylphenylimino)pentan-3-one nickel dibromide (Initiator 2)

The synthesis of initiator 2 was carried out according to Scheme 2 under an inert atmosphere. All reagents were dried, by various methods, prior to use. To a stirring suspension of (1,2-dimethoxyethane)NiBr$_2$ complex (82.0 mg, 0.266 mmol) in 15 mL methylene chloride, 2,4-bis(2-isopropyl-6-methylphenylimino)pentan-3-one (100 mg, 0.266 mmol) (prepared in a procedure similar to that shown in Example 1), in 5 ml methylene chloride, was added at once, at room temperature. Shortly after the addition of the ligand, the solution began to turn red. The suspension was allowed to stir for an additional 2.5 hours at room temperature. The reaction mixture was then filtered through celite and the solvent removed in vacuo. The corresponding red powder was washed with cold diethyl ether (−35° C., 3×, 10 mL), dried, resuspended in methylene chloride (10 mL), refiltered through celite and then dried to give the pure compound as a red powder in 82.0% yield (130.0 mg, 0.218 mmol). Anal. Calc. ($C_{25}H_{32}N_2$) C, 50.46; H, 5.42; N, 4.71. Found: C, 52.38; H, 5.67; N, 4.80.

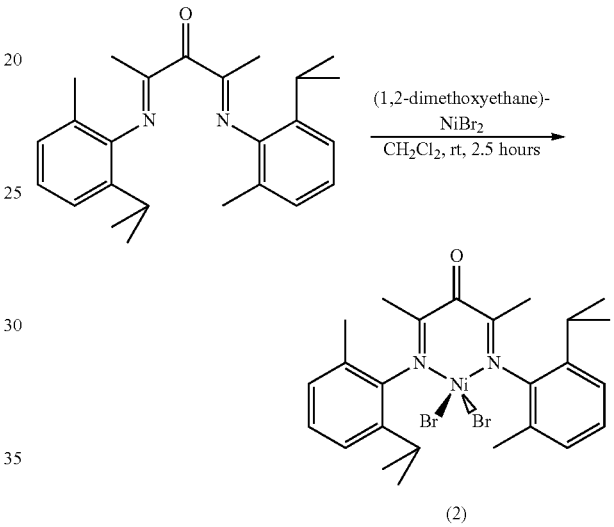

Scheme 2

EXAMPLE 9

Polymerization of Ethylene with Initiator 2

Homopolymerizations of ethylene were conducted in the following manner using initiator 2. A 300 mL steel autoclave reactor, equipped with an addition funnel was loaded, inside a glovebox with initiator 2 in 90 mL of toluene. MAO (Aldrich, 10 wt. % in toluene) was added to the addition funnel followed by toluene so that the final volume was 10 mL. The reactor was sealed inside the glovebox and attached to an ethylene line. The reactor was pre-pressurized with ethylene. The MAO solution was then injected under a specified pressure of ethylene, which was fed continuously at that pressure over the course of the reaction. Ethylene was vented after a specified amount of time and acidified methanol (10% HCl) was added to quench the polymerization. The precipitated polymer was collected by filtration, washed copiously with methanol, followed by acetone and dried under high vacuum overnight. Polymerization activities were calculated from the mass of the product obtained. Polymers were characterized by GPC analysis, relative to polystyrene standards, at 135° C. in o-dichlorobenzene (in a Polymer Laboratories, high-temperature chromatograph, Pl-GPC 200). Polymer melting points were measured on a TA instruments differential scanning calorimeter, (model DSC 2920) at a rate of 10° C./min for three cycles using a temperature range of 0-180° C. Table 5 below shows selected polymerization data.

TABLE 5

Selected Ethylene Homopolymerization Reactions with Initiator 2

| Initiator | Conc [μmol] | Cocatalyst [eq. MAO] | Ethylene [psi] | Temp. [° C.] | Activity[a] | $M_n \times 10^3$ | $M_w \times 10^3$ | PDI | $T_m$ [° C.] |
|---|---|---|---|---|---|---|---|---|---|
| 2 | 5 | 250 | 300 | 33 | 1366 | 792 | 1184 | 1.49 | — |
| 2 | 5 | 250 | 300 | 36 | 1873 | 868 | 1285 | 1.48 | — |

[a] Activity = (kg P/mol Ni hr)

EXAMPLE 10

Low Temperature Polymerization of Propene

Homopolymerizations of propene were conducted in the following manner using initiator 2. A 300 mL steel autoclave reactor, equipped with an addition funnel was loaded, inside a glovebox with initiator 2 in 90 mL of toluene. MAO (Aldrich, 10 wt. % in toluene) was added to the addition funnel followed by toluene so that the final volume was 10 mL. The reactor was sealed inside the glovebox and attached to a propene line. Propene was condensed for five minutes at 0° C. The reactor was then cooled to the desired temperature and the MAO solution was then injected. Propene was vented after a specified amount of time and acidified methanol (10% HCl) was added to quench the polymerization. The precipitated polymer was collected by centrifugation, washed copiously with methanol, followed by acetone and dried under high vacuum overnight. Polymerization activities were calculated from the mass of the product obtained. Polymers were characterized by GPC analysis, relative to polystyrene standards, at 135° C. in o-dichlorobenzene (in a Polymer Laboratories, high-temperature chromatograph, Pl-GPC 200). Glass transitions ($T_g$) and melting temperatures ($T_m$) were measured on a TA instruments differential scanning calorimeter, (model DSC 2920) at a rate of 5° C./min for three cycles using a temperature range of −70-180° C. Table 6 below shows selected polymerization data.

ethylene polymerization differing from that catalyzed by the analogous α-diimine complex (i.e. [ArN=C-(Me)C(Me)=NAr]NiBr$_2$ where Ar=2,6-diisopropylphenyl) in two significant ways: the polyethylene produced is more linear and complex 5 is a less active catalyst pre-cursor. In the reported example, a 100 mL autoclave reactor was charged with complex 5 (52 mg, 0.080 mmol) and flushed with ethylene. A solution of modified methyl aluminoxane (2.40 mL, 6.4 wt % Al in toluene from Akzo, 4.88 mmol) in 40 mL of toluene under nitrogen was then added. The reactor was pressurized with 280 psi of ethylene and stirred for 3.5 hr. The reaction temperature increased from 27 to 31° C. during this time and work-up afforded 4.07 g PE. ($T_m$ 120.2° C.). No molecular weight data was included. This corresponds to an activity of 14.5 (kg P/mol Ni hr).

Polymerization of Ethylene by Complex ArN=C(Me)-C(Me)=NAr)NiBr$_2$ (Ar=2,6-diisopropyl)/MAO at 25° C. was accomplished by adding standard catalyst solution (1.7 μmol catalyst) to a Schlenk flask which contained 100 mL toluene and was under 1 atmosphere of ethylene pressure. The solution was brought to the desired temperature and 1.0 mL of a 10% solution of MAO (~1000 eq) in toluene was added. The solution was stirred for 15 minutes. Polymer began to precipitate within minutes. The polymerization was quenched and the polymer precipitated from acetone. The resulting polymer was dried in vacuo to give 4.6 g PE. $M_w$=7.6×10$^{-4}$, $M_n$=3.1×10$^{-4}$. Activity=11000 kg of PE mol$^{-1}$ of Ni h$^{-1}$.

TABLE 6

Selected Propene Homopolymerization Reactions with Initiator 2

| Initiator | Conc [μmol] | Cocatalyst [eq. MAO] | Temp. [° C.] | Activity[a] | $M_n \times 10^3$ | $M_w \times 10^3$ | PDI | $T_m$ [° C.] | $T_g$ [° C.] |
|---|---|---|---|---|---|---|---|---|---|
| 2 | 20 | 250 | 0 | 5 | 73 | 83 | 1.13 | — | −22 |
| 2 | 20 | 250 | −30 | 1 | 12 | 99 | 8.23 | 113 | −28 |

[a] Activity = (kg P/mol Ni hr)

Figure 7:
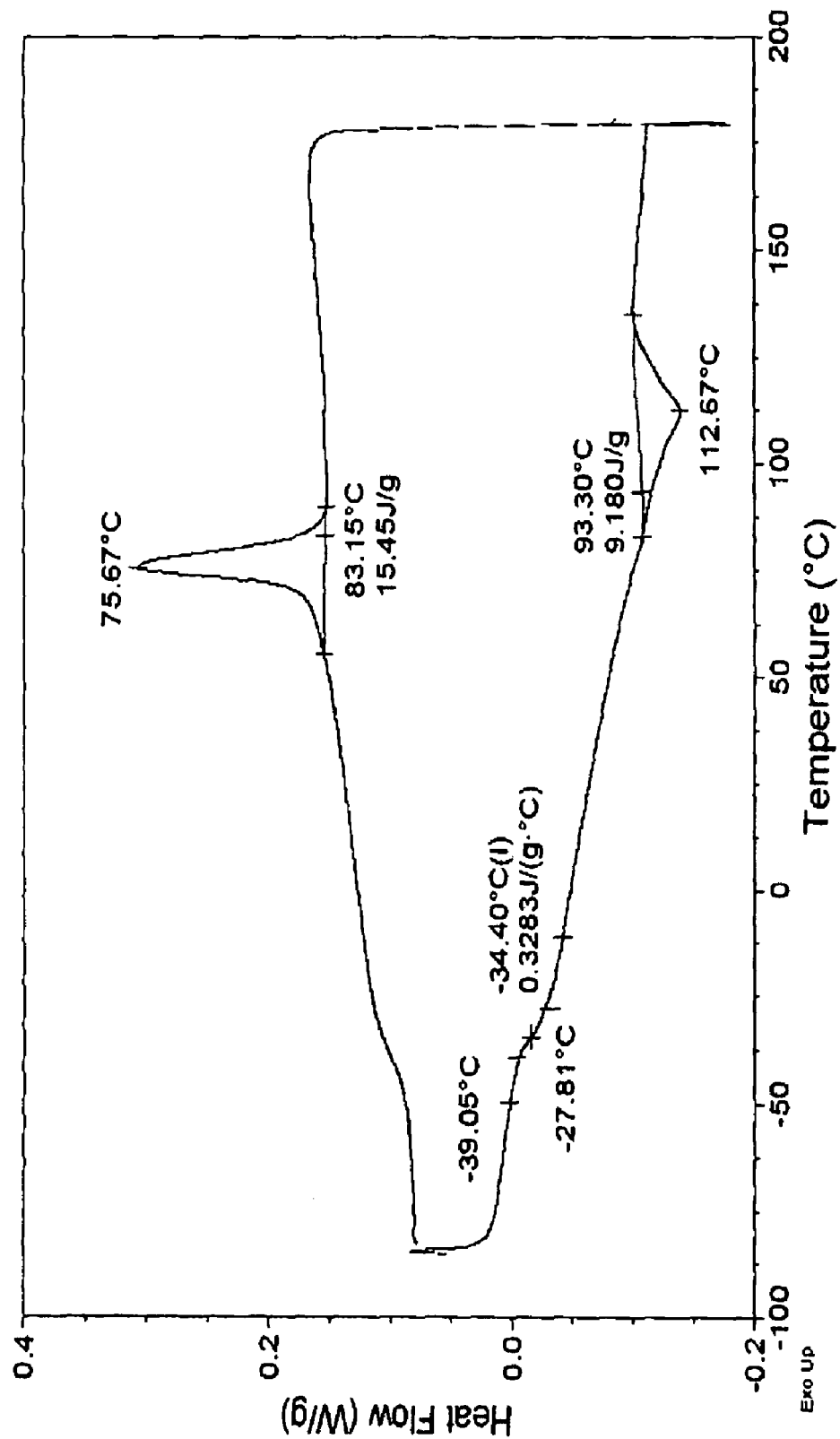
FIG. 7 is a differential scanning calorimetry trace of a semicrystalline polypropylene.

FIG. 7 shows a differential scanning calorimetry generated graph for entry 2 in Table 6 above. The melting temperature ($T_m$) and corresponding crystallization temperature ($T_c$) indicate the transition from a purely amorphous polymer to a polymer with some crystallinity based on the symmetry of the ligand and the reaction conditions. This illustrates that the microstructure can be controlled based on the choice of ligand and the corresponding reaction conditions.

EXAMPLE 11

Comparative Examples

In order to illustrate the importance of the ketone functionality on the ligand the following comparative example is included. Complex 5 (ArN=C-(Me)CH$_2$C(Me)=NAr]NiBr$_2$ where Ar=2,6-diisopropylphenyl) (46) is the corresponding β-diimine complex of NI(II) lacking a ketone functionality on the backbone (C(3) in FIG. 1). Complex 5 is a precursor for

Living Polymerization

Examples 12-15 relate to living polymerization reactions. Example 12 describes the results of polymerization reactions, while Examples 13-15 provide supporting information for the results described in Example 12.

EXAMPLE 12

Living Polymerization Using Initiator 1

Starting with the previously reported reactivity of initiator 1/MAO, the polydispersity (PDI) of the PE products was noted to decrease with decreasing reaction temperature ($T_{rxn}$) (57). To assess whether the active species could polymerize ethylene in a living manner, the volatiles from commercially available MAO were removed in vacuo until a free flowing white powder was obtained. This treatment is commonly utilized to remove free TMA, which may participate in termination and chain transfer reactions (58). A series of polymerizations were carried out to probe the effect of $T_{rxn}$ and ethylene pressure ($P_{C2H4}$). In these reactions, a 100 mL autoclave reactor was loaded with 40 mL toluene and MAO so that [Al]/[Ni]=250. A stock solution of initiator 1 was prepared and 1.5 μmol of Initiator (1) in approximately 1 mL $CH_2Cl_2$ was added to an addition funnel. The reactor and addition funnel were pre-pressurized with ethylene, cooled to the appropriate temperature, and the polymerization was initiated by introducing Initiator (1) under rapid stirring conditions. Ethylene was continually fed into the reactor over the course of the polymerization, and the reaction terminated by quenching with methanol or triethylsilane.

Figure 8:
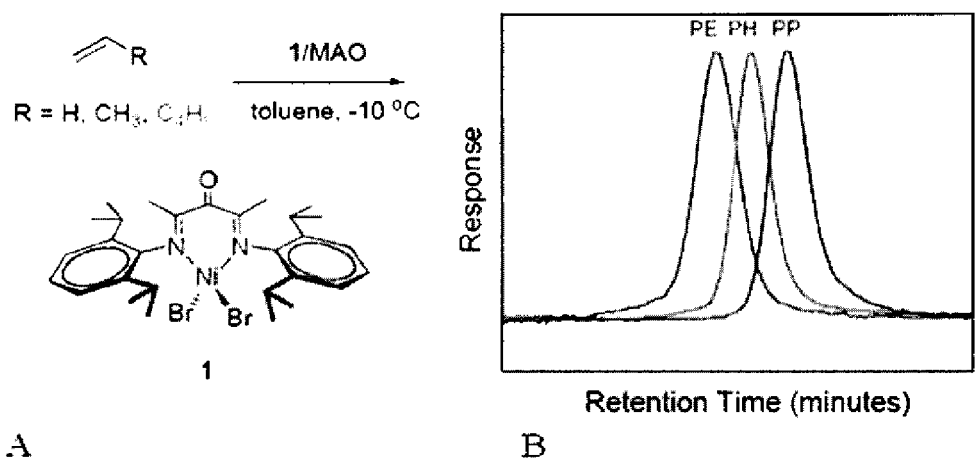
FIG. 8A is a scheme showing the synthesis of polyethylene (PE), polypropylene (PP) and poly(1-hexene) with symmetric GPC traces and polydispersities less than 1.1 using initiator 1/MAO at low temperatures.
FIG. 8B is a graph showing GPC traces for various polymers.

Table 7 summarizes the results of the initial screening study. Comparison of entries 1 and 2 demonstrates that reducing $T_{rxn}$ from 20° C. to 10° C. while keeping $P_{C2H4}$ constant at 300 psi leads to a narrowing of the PDI (1.60 vs. 1.35), as determined by gel permeation chromatography (GPC) calibrated against polystyrene standards. Reducing $P_{C2H4}$ to 150 psi at $T_{rxn}$=10° C., leads to further narrowing of the PDI to 1.22, as shown in entry 3. At $T_{rxn}$=−10° C. at $P_{C2H4}$=150 psi, a PE with PDI=1.09 was obtained (entry 4). Under the same conditions, when the polymerization is allowed to proceed for 20 minutes instead of 10 minutes, the molecular weight increases by approximately a factor of two (entry 4 vs. 5). Entry 6 shows that reducing $P_{C2H4}$ to 50 psi yields a PE with properties nearly identical to those obtained with $P_{C2H4}$=150 psi (entry 4) in terms of PDI, number average molecular weight ($M_n$) and melting point ($T_m$), but with a more symmetric GPC peak shape than in entry 4 (see Examples 13..., below). The effect of the quenching agent and method is demonstrated by comparing entry 6 (methanol) with entry 7 (triethylsilane). While the data in Table 7 show that the product properties are indistinguishable, the GPC traces after quenching with methanol contain a small shoulder of high molecular weight product, which is absent after quenching with triethylsilane. For this reason, triethylsilane was utilized in subsequent reactions. Entry 8 shows that excellent control over the molecular weight characteristics can be obtained after 60 minutes; the reaction scheme and GPC trace of this product are shown in FIGS. 8A and 8B, respectively. This PE displays a melting temperature ($T_m$) of 122° C. and a crystallinity ($\chi_c$) of 32%, despite the low ethylene pressure ($P_{C2H4}$=50 psi).

TABLE 7

Polymerization reactions

| Entry | Monomer | $t^a$ | $T^b$ | $TOF^c$ | $M_n^d$ | PDI | $T_m, T_g^e$ |
|---|---|---|---|---|---|---|---|
| 1 | E (300 psi) | 10 | 20 | 53 | 450 | 1.60 | 113 |
| 2 | E (300 psi) | 10 | 10 | 29 | 260 | 1.35 | 122 |
| 3 | E (150 psi) | 10 | 10 | 22 | 216 | 1.22 | 115 |
| 4 | E (150 psi) | 10 | −10 | 4.9 | 36 | 1.09 | 127 |
| 5 | E (150 psi) | 20 | −10 | 5.6 | 61 | 1.12 | 129 |
| 6 | E (50 psi) | 10 | −10 | 5.2 | 33 | 1.12 | 126 |
| 7 | E (50 psi) | 10 | −10 | 5.6 | 35 | 1.09 | 125 |
| $8^f$ | E (50 psi) | 60 | −10 | 5.8 | 183 | 1.10 | 122 |
| 9 | P (5 mL) | 120 | −10 | 0.4 | 79 | 1.05 | 59, −24 ($T_g$) |
| 10 | H (15 mL) | 120 | −10 | 0.3 | 120 | 1.05 | −62 ($T_g$) |

$^a$Reaction time (minutes);
$^b$temperature (° C.);
$^c$turnover frequency (TOF) × $10^{-3}$ $h^{-1}$;
$^d M_n \times 10^{-3}$ g $mol^{-1}$ determined by GPC in o-dichlorobenzene at 135° C.,
$^e T_m$ unless otherwise noted and $T_g$, as determined by DSC in ° C.;
$^f$0.75 μmol of 1 was used in this reaction.

FIG. 8B shows GPC traces for PE, PP and PH under the conditions in Table 7, entries 8, 9 and 10, respectively.

Figure 9:
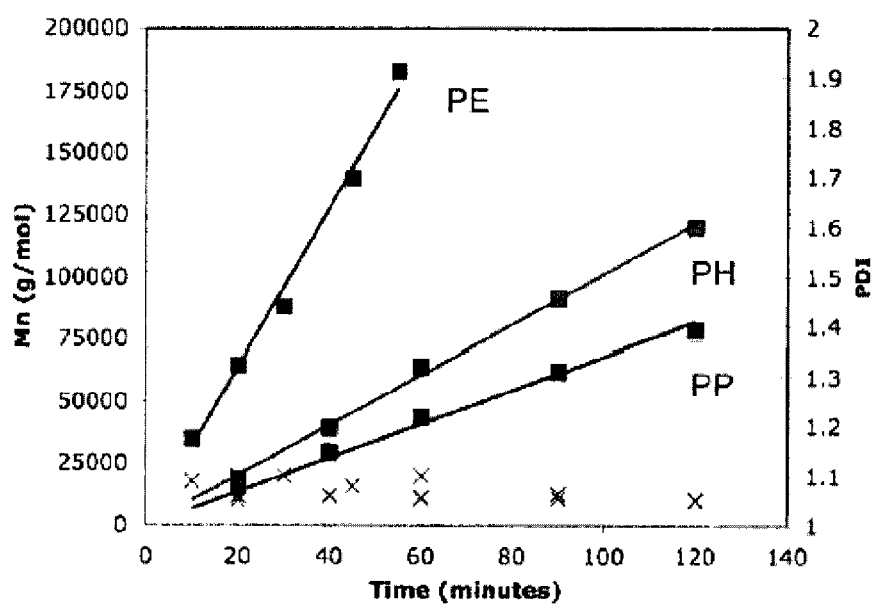
FIG. 9 shows a plot of M$_n$ versus time for various polymers.

FIG. 9 shows a plot of $M_n$ versus time under the same conditions as in entry 7 ($M_n$ (■) and PDI (x) versus time using initiator 1/MAO at −10° C. for PE, PP and PH determined by GPC). The linear growth of $M_n$ as a function of time and PDI values≦1.10, together with the results in Table 7, are consistent with the formation of semicrystalline PE under living conditions. The initiator 1/MAO combination can also be used to polymerize propene under living conditions. These reactions involved condensing 5 mL of propene into a 300 mL reactor loaded with 100 mL toluene and MAO so that [Al]/[Ni]=250. The reaction was cooled to −10° C. and the polymerization was initiated by the introduction of 10 μmol of initiator 1. Entry 9 in Table 7 shows the results for the PP obtained after 120 minutes of reaction; the GPC trace of this product is shown in FIG. 8B. Aliquots taken over the course of the polymerization show a linear relationship of $M_n$ as a function of time, as shown in FIG. 9. These characteristics, coupled with PDI values below 1.06, are indicative of a living polymerization. A melting transition was observed at $T_m$=59° C. and a degree of crystallinity of ~9%.

Reactions with 1'-hexene were carried out with [1-hexene]= 0.85 M under conditions similar to those in entry 9. The polymerization was sampled over the course of the reaction and examination of the products shows a linear increase of $M_n$ versus time and low PDI values, as shown in FIG. 9. Table 7, entry 10 contains results for the polymer generated at 120 minutes; the GPC trace of this product is shown in FIG. 8B. DSC analysis reveals that the polymer produced is amorphous ($T_g$=−62.0° C.).

The method described herein provides conditions that allow for the living polymerization of ethylene and α-olefins by using initiator 1/MAO. This is apparently the first late metal system that can polymerize ethylene in a living manner to afford semicrystalline PE, in contrast to quasi-living polymerization such as that in Diamanti et al. (25). This excellent control is remarkable given the fact that the PE precipitates over the course of the reaction. Additionally, it is interesting to note that the PP produced contains isotactic sequences. These results are in contrast to other late metal systems that generally yield amorphous and atactic PP in the absence of chiral ligands (54; also, for partially isotactic PP ([mm]=0.41) using an α-diimine Ni(II) system, see Pappalardo, D. et al. (63)), or induce syndiotactic enchainment at lower temperatures (64). Increasing the size of the monomer to 1-hexene results in a loss of stereocontrol.

EXAMPLE 13

All manipulations of air and/or water sensitive compounds were performed under an inert atmosphere using standard glove box and Schlenk-line techniques. Dichloromethane ($CH_2Cl_2$) was distilled from $CaH_2$ and 1-hexene from Na/K alloy. Toluene was purchased from Aldrich (anhydrous grade) and used as received. MAO (methylaluminoxane solution, 10 wt. % in toluene) was purchased from Aldrich and dried in vacuo, until a free flowing white powder was obtained. Ethylene (99.99%) and propene (99.97%) were purchased from Matheson Trigas and purified by passing through Agilent moisture and oxygen traps. Initiator 1 was synthesized as previously reported (57). Reagents, unless otherwise specified, were purchased from Aldrich and used without further purification. Polymerization activities were calculated from the mass of the product obtained. Polymers were characterized by GPC analysis, relative to polystyrene standards, at 135° C. in o-dichlorobenzene (in a Varian Polymer Laboratories, high-temperature chromatograph, PL GPC 220). Polymer melting points ($T_m$) and glass transition temperatures ($T_g$) were measured on a TA Instruments differential scanning calorimeter (model Q-20) at a rate of 10° C./min for three cycles using a temperature range of −70 to 180° C.

EXAMPLE 14

Polymerization of Ethylene: A 100 mL Parr steel autoclave reactor, equipped with an addition funnel, was loaded inside a glovebox with toluene (40 mL) and solid MAO so that [Al]/[Ni]=250 (22 mg, 0.375 mmol). A stock solution of initiator 1 was prepared and 1.5 μmol of initiator 1 in approximately 1 mL $CH_2Cl_2$ was added to the addition funnel. In Table 8 entry 8, 0.75 μmol of initiator 1 in approximately 1 mL $CH_2Cl_2$ was added to the addition funnel. An [Al]/[Ni]=250 (11 mg, 0.188 mmol) was maintained in this reaction. The reactor was sealed inside the glovebox and attached to an ethylene line. The addition funnel was pre-pressurized with ethylene at 50 psi above the desired reaction pressure with ethylene. The reactor was pre-pressurized to ($P_{C2H4}$) with ethylene and cooled to the appropriate reaction temperature ($T_{rxn}$). The polymerization was initiated via injection of the solution of initiator 1 and ethylene was continually fed into the reactor over the course of the reaction. The reaction temperature ($T_{rxn}$) was controlled using a dry-ice/acetone bath and found to be ±2° C. as monitored by an internal thermocouple. Ethylene was vented after a specified amount of time, and methanol was added to quench the polymerization (entries 1-6). The polymer was precipitated with methanol and was collected by filtration and washed with acidified methanol (10% HCl), methanol and acetone sequentially and dried under high vacuum to constant weight. The activity of the polymerization was calculated from the mass of the product obtained. In reactions utilizing triethylsilane ($Et_3SiH$) as the quenching agent (Table 7, entries 7 & 8 and Table 8), 1 mL $Et_3SiH$ in 2 mL of toluene was added to the addition funnel following introduction of the initiator stock solution. The addition funnel was pre-pressurized with ethylene at 50 psi above the desired reaction pressure ($P_{C2H4}$) and the solution injected into the rapidly stirring reaction mixture at the appropriate time point.

TABLE 8

Living Polymerization of Ethylene.

| Entry/ μmol Initiator 1 | Time (min.) | Temp. (° C.) | $M_n$ (g mol$^{-1}$) | PDI ($M_w/M_n$) | $T_m$ (° C.) |
|---|---|---|---|---|---|
| 1/1.5 | 10 | −10 | 35000 | 1.09 | 125 |
| 2/1.5 | 20 | −10 | 65000 | 1.10 | 125 |
| 3/1.5 | 30 | −10 | 88000 | 1.10 | 124 |
| 4/1.5 | 45 | −10 | 140000 | 1.08 | 123 |
| 5/0.75 | 60 | −10 | 183000 | 1.10 | 122 |

EXAMPLE 15

Living Polymerization of Propene: A 300 mL Parr steel autoclave reactor, equipped with an addition funnel, was loaded inside a glovebox with toluene (100 mL) and solid MAO so that [Al]/[Ni]=250 (145 mg, 2.50 mmol). A stock solution of initiator 1 was prepared and 10 μmol of initiator 1 in approximately 1 mL $CH_2Cl_2$ was added to the addition funnel. The reactor was sealed inside the glovebox. The reactor was cooled in a dry-ice/acetone bath and 5 mL propene was transferred into the reactor. The reactor was brought to the appropriate reaction temperature ($T_{rxn}$) and the polymerization was initiated via injection of the solution of initiator 1 under argon. The reaction temperature ($T_{rxn}$) was controlled by means of a dry-ice/acetone bath and found to be ±2° C. as monitored by an internal thermocouple. In order to monitor the number average molecular weight ($M_n$) and polydispersity (PDI) of the product with time; 5.0 mL aliquots of the polymerization solution were taken at 20, 40, 60 and 90 minutes under a flow of argon using a gas-tight syringe. The contents of the syringe were immediately quenched with methanol. Volatiles were removed in-vacuo and the residue washed with acidified methanol (10% HCl), methanol and acetone sequentially and dried under high vacuum. The remaining residue was dissolved in approximately S grams of o-dichlorobenzene by heating the contents to 135° C. with agitation. Gel permeation chromatography (GPC) of this solution was used to obtain the $M_n$ and PDI of each polymer sample, as shown in Table 9. The reaction at a time of 120 minutes was quenched by loading the addition funnel with methanol (5 mL) and injecting the methanol, under argon, directly into the stirring reaction mixture. The polymer was precipitated with methanol and was collected by filtration and washed with acidified methanol (10% HCl), methanol and acetone sequentially and dried under high vacuum to constant weight. The activity of the polymerization was calculated from the mass of the product obtained.

TABLE 9

GPC Results of Aliquots of the Polymerization Solution.

| Aliquot | Time (minutes) | $M_n$ (g mol$^{-1}$) | PDI |
|---|---|---|---|
| 1 | 20 | 16000 | 1.06 |
| 2 | 40 | 30000 | 1.06 |
| 3 | 60 | 44000 | 1.06 |
| 4 | 90 | 62000 | 1.06 |
| 5 | 120 | 79000 | 1.05 |

EXAMPLE 16

Living Polymerization of 1-hexene: A 300 mL Parr steel autoclave reactor, equipped with an addition funnel, was loaded inside a glovebox with toluene (125 mL), 1-hexene (15 mL, 120.0 mmol) and solid MAO so that [Al]/[Ni]=250 (181.3 mg, 3.13 mmol). A stock solution of initiator 1 was prepared and 12.5 μmol of initiator 1 in approximately 1 mL $CH_2Cl_2$ was added to the addition funnel. The reactor was sealed inside the glovebox and cooled in a dry-ice/acetone bath to the appropriate reaction temperature ($T_{rxn}$). The polymerization was initiated via injection of the solution of initiator 1 under argon. The reaction temperature ($T_{rxn}$) was controlled by means of a dry-ice/acetone bath and found to be ±2° C. as monitored by an internal thermocouple. In order to monitor the number average molecular weight ($M_n$) and polydispersity (PDI) of the product with time; 5.0 mL aliquots of the polymerization solution were taken at 20, 40, 60 and 90 minutes under a flow of argon using a gas-tight syringe. The contents of the syringe were immediately quenched with methanol. Volatiles were removed in-vacuo and the residue washed with acidified methanol (10% HCl), methanol and acetone sequentially and dried under high vacuum. The remaining residue was dissolved in approximately 5 grams of o-dichlorobenzene by heating the contents to 135° C. with agitation. Gel permeation chromatography (GPC) of this solution was used to obtain the $M_n$ and PDI of each polymer sample as shown in Table 10. The reaction at a time of 120 minutes was quenched by loading the addition funnel with methanol (5 mL) and injecting the methanol, under argon, directly into the stirring reaction mixture. The polymer was precipitated with methanol and the precipitated polymer collected by filtration and washed with acidified methanol (10% HCl), methanol and acetone sequentially and dried under high vacuum to constant weight. The activity of the polymerization was calculated from the mass of the product obtained.

TABLE 10

GPC Results of Aliquots of the Polymerization Solution.

| Aliquot | Time (minutes) | $M_n$ (g mol$^{-1}$) | PDI |
|---|---|---|---|
| 1 | 20 | 19000 | 1.05 |
| 2 | 40 | 40000 | 1.06 |
| 3 | 60 | 65000 | 1.05 |
| 4 | 90 | 91000 | 1.06 |
| 5 | 120 | 120000 | 1.05 |

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the claims.

REFERENCES

The following publications are incorporated by reference herein.
1. B. Rieger, L. Baugh, S. Striegler, S. Kacker, *Late Transition Metal Catlysis*, John Wiley & Sons, New York, 2003.
2. R. Blom, A. Follestad, E. Rytter, M. Tilset, M. Ystenes, *Organometallic Catalysts and Olefin Polymerization: Catalysts for a New Millenium*, Springer-Verlag, Berlin, Germany, 2001.
3. S. D. Ittel, L. K. Johnson, M. Brookhart, *Chem. Rev.* 2000, 100, 1169-1203.
4. L. S. Boffa, B. M. Novak, *Chem. Rev.* 2000, 100, 1479-1493.
5. M. J. Yanjarappa, S. Sivaram, *Prog. Polym. Sci.* 2002, 27, 1347-1398.
6. S. Mecking, A. Held, F. M. Bauers, *Angew. Chem., Int. Ed.* 2002, 41, 544-561.
7. V. C. Gibson, S. K. Spitzmesser, *Chem. Rev.* 2003, 103, 283-315.
8. Mitani, M.; Furuyama, R.; Mohri, J.-I.; Saito, J.; Ishii, S.; Terao, H.; Nakano, T.; Tanaka, H.; Fujita, T. *J. Am. Chem. Soc.* 2003, 125, 4293.
9. Saito, J.; Mitani, M.; Onda, M.; Mohri, J.-I.; Ishii, S.-I.; Yoshida, Y.; Nakano, T. H.; Tanaka, T.; Kojoh, S.-I.; Kashiwa, N.; Fujita, T. *Macromol Rapid Commun.* 2001, 22, 1072.
10. Kleinschmidt, R.; Griebenow, Y.; Fink, G. *Journal of Molecular Catalysis A: Chemical* 2000, 157, 83.
11. Pellecchia, C.; Mazzeo, M.; Pappalardo, D. *Macromol. Rapid Commun.* 1998, 19, 651.
12. Obera, Y.; Stern, C. L.; Marks, T. J. *Organometallics* 1997, 16, 2503.
13. Guerra, G.; Longo, P.; Cavallo, L.; Corradini, P.; Resconi, L. *J. Am. Chem. Soc.* 1997, 119, 4394.
14. Hagimoto, H.; Shiono, T.; Ikeda, T. *Macromolecules*, 2002, 35, 5744.
15. Choo, T. N.; Waymouth, R. M. *J. Am. Chem. Soc.* 2002, 124, 4188.
16. Nomura, K.; Oya, K.; Imanishi, Y. *Journal of Molecular Catalysis A: Chemical* 2001, 174, 127.
17. Schaverien, C. J.; Ernst, R.; Schut, P.; Dall'Occo, T. *Organometallics* 2001, 20, 3436.
18. J. M. Rose, A. E. Cherian, G. W. Coates, *J. Am. Chem. Soc.* 2006, 128, 4186-4187.
19. Johnson, L. K.; Mecking, S.; Brookhart, M. *J. Am. Chem. Soc.* 1996, 118, 267.
20. Mecking, S.; Johnson, L. K.; Wang, L.; Brookhart, M.; *J. Am. Chem. Soc.* 1998, 120, 888.
21. Younkin, T. R.; Connor, E. F.; Henderson, J. I.; Freidrich, S. K.; Grubbs, R. H.; Bansleben, D. A. *Science* 2000, 287, 460.
22. Connor, E. F.; Younkin, T. R.; Henderson, J. I.; Hwang, S.; Grubbs, R. H.; Roberts, W. P.; Litzau, J. J. *J Polym Sci. Part A: Polym. Chem.* 2002, 40, 2842.
23. Benedikt, G. M.; Elce, E.; Goodall, B. L.; Kalamarides, H. A.; McIntosh, L. H. III; Rhodes, L. F.; Selvy, K. T.; Andes, C.; Oyler, K.; Sen, A. *Macromolecules* 2002, 35, 8978.
24. Gottfried, A. C.; Brookhart, M. *Macromolecules*, 2003, 36, 3085.
25. S. J. Diamanti, P. Ghosh, F. Shimizu, G. C. Bazan, *Macromolecules* 2003, 36, 9731-9735.
26. S. J. Diamanti, V. Khanna, A. Hotta, D. Yamakawa, F. Shimizu, E. J. Kramer, G. H. Frederickson, G. C. Bazan, *J. Am. Chem. Soc.* 2004, 126, 10528-10529.
27. R. C. Coffin, S. J. Diamanti, A. Hotta, V. Khanna, E. J. Kramer, G. H. Fredrickson, G. C. Bazan, *Chem. Commun.* 2007, 3550-3552.
28. Younkin, T. R.; Connor, E. F.; Henderson, J. I.; Freidrich, S. K.; Grubbs, R. H.; Bansleben, D. A. *Science* 2000, 287, 460.
29. Mohring V. M.; Fink G. *Angew. Chem., Int. Ed. Engl.* 1985, 24, 1001.
30. Guan Z.; Cotts P. M.; McCord E. F.; McClain S. J. *Science* 1999, 283, 2059-2062.
31. Rose J. M.; Cherian A. E.; Coates G. W. *J. Am. Chem. Soc.* 2006, 128, 4186-4187.
32. Held A.; Bauers F. M.; Mecking S. *Chem. Commun.* 2000, 301-302.
33. Bauers F. M.; Mecking S. *Macromolecules* 2001, 34, 1165-1171.
34. Korthals B.; Schnetmann I. G.; Mecking S. *Organometallics* 2007, 26, 1311-1316.
35. Bonnet, M. C.; Dahan, F.; Ecke, A.; Keim, W.; Schultz, R. P.; Tkatchenko, I. J. *J. Chem. Soc., Chem. Commun.* 1994, 615-616.
36. Komon, Z. J.; Bu, X.; Bazan, G. C. *J. Am. Chem. Soc.* 2000, 122, 1830-1831.
37. Komon, Z. J.; Bu, X.; Bazan, G. C. *J. Am. Chem. Soc.* 2000, 122, 12379-12380.
38. Lee, B. Y.; Bazan, G. C.; Vela, J; Komon, Z. J.; Bu, X. *J. Am. Chem. Soc.* 2001, 123, 5352-5353.
39. Chen, Y.; Wu, G.; Bazan, G. C. *Angew. Chem., Int. Ed. Engl.* 2005, 44, 1108-1112.
40. Kwon, H. Y.; Lee, S. Y.; Lee, B. Y.; Shin, D. M.; Chung, Y. K. *Dalton Transactions* 2004, 921-928.
41. Shim, C. B.; Kim, Y. H.; Lee, B. Y.; Shin, D. M; Chung, Y. K. *J. Organomet. Chem.* 2003, 675, 72-76.
42. Kim, Y. H.; Kim, T. H.; Lee, B. Y.; Woodmandee, D.; Bu, X; Bazan, G. C. *Organometallics* 2002, 21, 3082-3084.
43. Shim, C. B.; Kim, Y. H.; Lee, B. Y.; Dong, Y.; Yun. H. *Organometallics* 2003, 22, 4272-4280.
44. Lee, B. Y.; Bu, X., Bazan, G. C. *Organometallics* 2001, 20, 5425-5431.
45. S. Yokota, Y. Tachi, S. Itoh *Inorg. Chem.* 2002, 41, 1342-1344.
46. J. Feldman, S. J. McLain, A. Parthasarathy, W. J. Marshall, J. C. Calabrese, S. D. Arthur, *Organometallics* 1997, 16, 1514-1516.

47. Domski, G. J.; Rose, J. M.; Coates, G. W.; Bolig, A. D.; Brookhart, M. *Prog. Polym. Sci.* 2007, 32, 30-92.
48. Coates, G. W.; Hustad, P. D.; Reinartz, S. *Angew. Chem., Int. Ed. Engl.* 2002, 41, 2237-2257.
49. Johnson, L. K.; Mecking, S.; Brookhart, M. *J. Am. Chem. Soc.* 1996, 118, 267-268.
50. Berkefeld, A.; Mecking, S. *Angew. Chem. Int. Ed.* 2008, 47, 2-7.
51. Johnson, L. K.; Killian, C. M.; Brookhart, M. *J. Am. Chem. Soc.* 1995; 117, 6414-6415.
52. Leatherman, M. D.; Svedja, S. A; Johnson, L. K.; Brookhart, M. *J. Am. Chem. Soc.* 2003, 125, 3068-3081.
53. Meinhard, D.; Wegner, M.; Kipiani, G.; Hearley, A.; Reuter, P.; Fischer, S.; Marti, O.; Rieger, B. *J. Am. Chem. Soc.* 2007, 129, 9182-9191.
54. Killian, C. M.; Tempel, D. J.; Johnson, L. K.; Brookhart, M. *J. Am. Chem. Soc.* 1996, 118, 11664-11665.
55. Cherian, A. E.; Rose, J. M.; Lobkovsky, E. B.; Coates, G. W.; *J. Am. Chem. Soc.* 2005, 127, 13770-1377.
56. Rose, J. M.; Deplace, F.; Lynd, N. A.; Wang, Z.; Hotta, A.; Lobkovsky, E. B. Kramer, E. J; Coates, G. W. *Macromolecules* 2008, 41, 9548-9555.
57. Azoulay, J. D.; Rojas, R. S.; Serrano, A. V.; Ohtaki, H.; Galland, G. B.; Bazan, G. C. *Angew. Chem., Int. Ed. Engl.* 2009, 48, 1089-1092.
58. Chen, E. Y-X.; Marks, T. J.; *Chem. Rev.* 2000, 100, 1391-1434.
59. Tian, J.; Hustad, D.; Coates, G. W. *J. Am. Chem. Soc.* 2001, 123, 5134-5135.
60. Mitani, M.; Furuyama, R.; Mohri, J-I.; Saito, J.; Ishii, S.-I.; Terao, H.; Kashiwa, N.; Fujita, T. *J. Am. Chem. Soc.* 2002, 124, 7888-7889.
61. Hasan, T.; Ioku, A.; Nishii, K.; Shiono, T.; Ikeda, T.; *Macromolecules* 2001, 34, 3142-3145.
62. Busico, V.; Cipullo, R.; Cutillo, F.; Friederichs, N.; Ronca, S.; Wang, B. *J. Am. Chem. Soc.* 2003, 125, 12402-12403.
63. Pappalardo, D.; Mazzeo, M.; Antinucci, S.; Pellechia, C. *Macromolecules* 2000, 33, 9483-9487.
64. Pellechia, C.; Zambelli, A.; *Macromol. Rapid. Commun.* 1996, 17, 333-338.
65. G. B. Galland, L. P. Da Silva, M. L. Dias, G. L. Crosetti, C. M. Ziglio, C. A. L. Filgueiras, *J Polym. Sci: Part A: Polym. Chem.* 2004, 42, 2171-2178.
66. F. F. N. Escher, G. B. Galland, *J. Polym. Sci. Part A: Polym. Chem.* 2004, 42, 2474-2482.
67. M. L. Dias, L. P. Da Silva, G. L. Crosetti, G. B. Galland, A. L. Filgueiras, C. M. Ziglio, *J Polym. Sci. Part A. Polym. Chem.* 2006, 44, 458-466.

What is claimed is:

1. An organometallic complex initiator, which is capable of polymerizing and copolymerizing olefins to high molecular weight polymers, according to the formula (I):

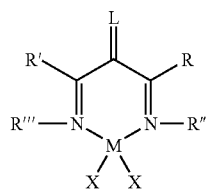

(I)

wherein:
R, R', R" and R'" are each independently an achiral or chiral alkyl or aryl group with or without one or more functional groups;

M is Fe, Co, Ni, Pd or Pt;

X is an alkyl, hydride or halide group; and

L is O, N—R"", S, or =CH$_2$, wherein R"" is an alkyl or aryl group.

2. The complex of claim 1, wherein R and R' are each alkyl, and R" and R'" are each aryl.

3. The complex of claim 1, wherein L is O.

4. The complex of claim 3, wherein R and R' are each alkyl, and R" and R'" are each aryl.

5. The complex of claim 4, wherein R and R' are each methyl.

6. The complex of claim 4, wherein R" and R'" are each 2,6-disubstituted aryl.

7. The complex of claim 1, wherein the complex is 2,4-bis(2,6-diisopropylphenylimino)pentan-3-one nickel dibromide or 2,4-bis(2-isopropyl-6-methylphenylimino)pentan-3-one nickel dibromide.

8. A process of producing an organometallic initiator complex, comprising mixing a metal compound with a ligand of the formula II:

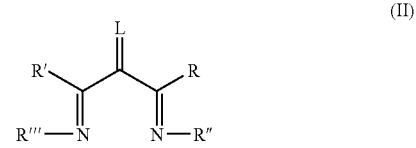

(II)

wherein R, R', R" and R'" are each independently an achiral or chiral alkyl or aryl group with or without one or more functional groups, and L is O, N—R"", S, or =CH$_2$, wherein R"" is an alkyl or aryl group.

9. The process of claim 8, wherein R and R' are each alkyl, and R" and R'" are each aryl.

10. The process of claim 8, wherein L is O.

11. The process of claim 10, wherein the R and R' are each alkyl, and R" and R'" are each aryl.

12. The process of claim 8, wherein R" and R'" are each 2,6-diisopropylphenyl or 2-isopropyl-6-methylphenyl.

13. The process of claim 8, wherein the metal compound is a metal halide complex.

14. The process of claim 13, wherein the metal compound is a (1,2-dimethoxyethane)NiBr$_2$ complex.

15. The process of claim 8, wherein the metal compound is an Fe, Co, Ni, Pd or Pt compound.

16. The process of claim 11, wherein R and R' are each methyl.

17. The process of claim 11, wherein R" and R'" are each 2,6-disubstituted aryl.

* * * * *